US009394390B2

(12) United States Patent
Faust et al.

(10) Patent No.: US 9,394,390 B2
(45) Date of Patent: Jul. 19, 2016

(54) COUMARIN-FUNCTIONALIZED POLYOLEFIN AND ASSOCIATED CYCLODIMERIZATION PRODUCTS, PREPARATION METHODS, AND ELECTRONIC DEVICES

(71) Applicant: University of Massachusetts, Boston, MA (US)

(72) Inventors: Rudolf Faust, Lexington, MA (US); Ranjan Tripathy, League City, TX (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 14/762,835

(22) PCT Filed: Feb. 6, 2014

(86) PCT No.: PCT/US2014/014982
§ 371 (c)(1),
(2) Date: Jul. 23, 2015

(87) PCT Pub. No.: WO2014/124072
PCT Pub. Date: Aug. 14, 2014

(65) Prior Publication Data
US 2015/0361195 A1 Dec. 17, 2015

Related U.S. Application Data

(60) Provisional application No. 61/762,176, filed on Feb. 7, 2013.

(51) Int. Cl.
*C08F 110/10* (2006.01)
*C07D 311/08* (2006.01)
(Continued)

(52) U.S. Cl.
CPC ............ *C08F 110/10* (2013.01); *C07D 311/08* (2013.01); *C08F 2/48* (2013.01); *H01L 51/004* (2013.01); *C08F 2810/40* (2013.01); *H01L 51/448* (2013.01); *H01L 51/5253* (2013.01)

(58) Field of Classification Search
None
See application file for complete search history.

(56) References Cited

U.S. PATENT DOCUMENTS 6,005,051 A  12/1999  Kennedy et al.
6,069,185 A  5/2000  Bahadur et al.
(Continued)

FOREIGN PATENT DOCUMENTS

WO  2006110647 A1  10/2006
WO  2010111280 A1  9/2010
WO  2012010360 A1  1/2012

OTHER PUBLICATIONS

Chen, Polymer, vol. 37, No. 20, pp. 4473-4480 (1996).*
(Continued)

*Primary Examiner* — Robert C Boyle
(74) *Attorney, Agent, or Firm* — Cantor Colburn LLP

(57) ABSTRACT

A polyolefin is functionalized with two, three, or more terminal coumarin groups. When irradiated with longer wavelength ultraviolet light (e.g., 365 nanometers), the coumarin groups cyclodimerize to form a chain-extended or crosslinked polyolefin. The cyclodimerization can be reversed by irradiation with shorter wavelength ultraviolet light (e.g., 254 nanometers). When the crosslinked polyolefin is used to form a barrier layer in a light emitting diode or a photovoltaic device, scratches in the barrier layer cleave the cyclodimer groups and can be "healed" by irradiation to reduce or remove the scratches.

14 Claims, 17 Drawing Sheets

(51) Int. Cl.
*C08F 2/48* (2006.01)
*H01L 51/00* (2006.01)
*H01L 51/44* (2006.01)
*H01L 51/52* (2006.01)

(56) References Cited

U.S. PATENT DOCUMENTS

| | | | |
|---|---|---|---|
| 6,423,818 B1 * | 7/2002 | Matsuda | A61L 27/18 522/1 |
| 6,942,926 B2 | 9/2005 | Liu et al. | |
| 7,569,694 B2 | 8/2009 | Koike et al. | |
| 2006/0264577 A1 | 11/2006 | Faust et al. | |
| 2010/0069578 A1 * | 3/2010 | Faust | C08F 8/26 525/384 |
| 2011/0086183 A1 | 4/2011 | Erlat et al. | |
| 2011/0315206 A1 | 12/2011 | Krajewski et al. | |
| 2012/0077934 A1 | 3/2012 | Faust et al. | |

OTHER PUBLICATIONS

Tian, Journal of Polymer Science: Part A: Polymer Chemistry, vol. 41, 2197-2206 (2003).*
Trenor, Chem. Rev., 2004, 104, 3059-3077.*
Cheng-Mei, Polymer Bulletin, 57, 139-149 (2006).*
He, J. et al "Photoinduced bending of a coumarin-containing supramolecular polymer", Soft Matter, 2009, vol. 5, pp. 308-310.
International Search Report mailed Nov. 18, 2014; International Application No. PCT/US2014/014982; International Filing Date Feb. 6, 2014 (5 pages).
Karthikeyan, S. et al., "Templating Photodimerizatoin of Coumarins within a Water-Soluble Nano Reaction Vessel", J. Org. Chem. 2006, vol. 71, pp. 6409-6413.
Kelly, S.M. et al., "Liquid Crystals for Electro-Optic Applications", Handbook of Advanced Electronic and Photonic Materials and Devices, edited by H.S. Nalwa, 2000, vol. 7: Liquid Crystals, Display and Laser Materials, Chapter 1, pp. 1-66.
Wang, Z-S. et al., "Thiophene-Functionalized Coumarin Dye for Efficient Dye-Sensitized Solar Cells: Electron Lifetime Improved by Coadsorption of Deoxycholic Acid", J. Phys. Chem. C. 2007, vol. 111, pp. 7224-7230.
Written Opinion mailed Nov. 18, 2014; International Application No. PCT/US2014/014982; International Filing Date Feb. 6, 2014 (6 pages).
Bergman, S.D., et al. "Mendable polymers" Journal of Materials Chemistry 2008, 18, pp. 41-62.
Brown, E.N., et al., "In Situ Poly(Urea-Formaldehyde) Microencapsulation of Dicylopentadiene" J. Microencapsulation, Nov.-Dec. 2003, vol. 20, No. 6, 719-730.
Cardoso, R.J., et al., "Effect of particle size and surface treatment on constitutive properties of polyester-cenosphere composites" Journal of Materials Science 37 (2002) 603-613.
Chen, X. et al., "New Thermally Remendable Highly Cross-Linked Polymeric Materials" Macromolecules (2003), 36, 1802-1807.
Chen, Y. et al, "Polyethers Containing Coumarin Dimer Components in the Main Chain. II. Reversible Photocleavage and Photopolymerization" Journal of Applied Polymer Science, 1997, vol. 64, 1759-1768.
Chen, Y. et al., "Copolymers derived from 7-acryloyloxy-4-methylcoumarin and acrylates: 1. Copolymerizability and photocrosslinking behaviours" Polymer 1996, vol. 37, No. 20, pp. 4473-4480.
Chen, Y. et al., "Photopolymerization of 7,7' -Coumarinyl Polymethylene Dicarboxylates: Fluorescence and Kinetic Study" Journal of Polymer Scient, Part A: Polymer Chemistry, 1997, vol. 35, 2999-3008.
Chen, Y. et al., "Polyethers Containing Coumarin Dimer Components in the Main Chain. I. Synthesis by Photopolymerization of 7,7'-(Polymethylenedioxy) dicoumarins", Journal of Applied Polymer Science, 1997, vol. 64 1749-1758.
Chen, Y., et al., "Synthesis and Reversible Photocleavage of Novel Polyurethanes Containing Coumarin Dimer Components" Journal of Polymer Science, Part A: Polymer Chemistry, 1997, vol. 35, pp. 613-624.
Chujo, Y., et al., "Plyoxazoline Having a Coumarin Moiety as a Pendant Group. Synthesis and Photogelation1" Macromolecules (1990) 23, 2693-2697.
Chung, C-M, et al., "Crack Healing in Polymeric Materials via Photochemical [2+2] Cycloaddition", Chem. Mater. 2004, vol. 16, pp. 3982-3984.
Chung, J.W. et al., "Photoresponsive Coumarin-Stabilized Polymeric Nanoparticles as a Detectable Drug Carrier", Small 2012, 8, No. 11, pp. 1693-1700.
Corten, C.C., et al. "Repairing Polymers Using an Oscillating Magnetic Field" Advanced Materials 2009, 21, pp. 5011-5015.
Elowe, et al., "Development of Direct Cell Inorganic Barrier Film Technology Providing Exceptional Device Stability for CIGS Solar Cells" Chemistry of Materials 2011, 23, 3915-3920.
Gaume, et al., "Photochemical Behavior of PVA as an Oxygen-Barrier Polymer for Solar Cell Encapsulation" RSC Advances, 2011, 1, pp. 1471-1481.
Hasegawa, M. et al., "Photocleavage of Coumarin Dimers", Chemistry Letters, 1972, pp. 317-320.
Huyck, et al., "Photodimerization of Coumarin Functionalized Poly(alkyl Acrylate) and Poly(alkyl Methacrylate) Random Copolymers: Influence of Copolymer Composition on Photocrosslinking" J. Macro. Sci. Part A: Pure and Applied Chemistry 2008, 40, 9-15.
Kamphaus, J.M., et al., "A new self-healing epoxy with tungsten (VI) chloride catalyst" Journal of the Royal Society Interface (2008) 5, 95-103.
Leenders, L.H. et al., "Photochemistry of Nonconjugated Bichromophoric Systems. Cyclomerization of 7,7'-Polymethylenedioxycoumarins and Polymethylenediarboxylic Acid (7-Coumarinyl) Diesters" J. Org. Chem., vol. 38, No. 5, (1973) 957-966.
Murphy, E.B., et al. "The world of smart healable materials" Progress in Polymer Science 35 (2010) pp. 223-251.
Pang, J.W.C., et al., "'Bleeding Composites'—Damage Detection and Self-repair Using a Biomimetic Approach", Compsites: Part A 36 (2005) pp. 183-188.
Pang, Jody W.C., et al., "A Hollow Fibre Reinforced Polymer Composite Encompassing Self-Healing and Enhanced Damage Visibility" Composites Science and Technology, 65 (2005) pp. 1791-1799.
Ramamurthy, V., et al., "Photochemical Reactions of Organic Crystals" Chem. Rev. 1987, 87, 433-481.
Ramasubbu, N., et al., "Photodimerization of Coumarins in the Solid State" J. Chem. Soc., Chem. Commun., 1982, 3, 178-179.
Tian, Q., et al., "A thermally remendable epoxy resin" Journal of Materials Chemistry 2009, 19, 1289-1296.
Trenor, S.R., et al., "Coumarins in Polymers: From Light Harvesting to Photo-Cross-Linkable Tissue Scaffolds" Chem. Rev. 2004, 104, pp. 3059-3077.
Trenor, S.R., et al., "Photoreversible Chain Extension of Poly(ethylene glycol)" Macromolecular Chemistry and Physics 2004, 205, 715-723.
Urban, M. W., "Stratification, stimuli-responsiveness, self-healing, and signaling in polymer networks" Progress in Polymer Science 34 (2009) 679-687.
Wu, D.Y., et al.,"Self-healing polymeric materials: A review of recent developments" Progress in Polymer Science 2008, 33, pp. 479-522.
Zhang, Y., et al., "Thermally Self-Healing Polymeric Materials: The Next Step to Recycling Thermoset Polymers?" Macromolecules 2009, 42, 1906-1912.
Zheng, Y. et al., "PEG-Based Hydrogel Synthesis via the Photodimerization of Anthracene Groups" Macromolecules 2002, 35, pp. 5228-5234.

* cited by examiner

COUMARIN-FUNCTIONALIZED POLYOLEFIN AND ASSOCIATED CYCLODIMERIZATION PRODUCTS, PREPARATION METHODS, AND ELECTRONIC DEVICES

BACKGROUND OF THE INVENTION

Self-healing polymeric materials have gained substantial importance in recent times due to its inherent ability to repair damages caused by mechanical deformations, corrosion by chemicals or degradation in adverse atmospheric conditions thus preventing catastrophic failure and increasing the life time of materials. See, e.g., E. B. Murphy, F. Wudl, *Progress in Polymer Science* 2010, 35, 223; C. C. Corten, M. W. Urban, *Advanced Materials* 2009, 21, 5011; M. W. Urban, *Progress in Polymer Science* 2009, 34, 679; S. D. Bergman, F. Wudl, *Journal of Materials Chemistry* 2008, 18, 41; and D. Y. Wu, S. Meure, D. Solomon, *Progress in Polymer Science* 2008, 33, 479. These adverse repetitive external stimuli result in formation of micro cracks or cavities eventually leading to macroscopic damage. Crack healing has been accomplished by wielding, incorporating hollow fibers or micro encapsulation of healing monomers and also by employing thermally reversible Diels-Alder reaction. See, e.g., J. W. C. Pang, I. P. Bond, *Composites Science and Technology* 2005, 65, 1791; J. W. C. Pang, I. P. Bond, *Composites Part A* 2005, 36, 183; J. M. Kamphaus, J. D. Rule, J. S. Moore, N. R. Sottos, S. R. White, *Journal of the Royal Society Interface* 2008, 5, 95; R. J. Cardoso, A. Shukla, *Journal of Materials Science* 2002, 37, 603; E. N. Brown, M. R. Kessler, N. R. Sottos, S. R. White, *Journal of Microencapsulation* 2003, 20, 719; X. Chen, F. Wudl, A. K. Mal, H. Shen, S. R. Nutt, *Macromolecules*, 2003, 36, 1802; Q. Tian, Y. C. Yuan, M. Z. Rong, M. Q. Zhang, *Journal of Materials Chemistry* 2009, 19, 1289; and Y. Zhang, A. A. Broekhuis, F. Picchioni, *Macromolecules* 2009, 42, 1906. However, reversible photocyclizations are of great commercial importance due to their capability to heal repeated damage at the same position. Moreover, these photoreactions are inexpensive and environmentally friendly alternative to harsh reagents in order to enact chemical transformations.

Olefin compounds such as cinnamic acid, anthracene, thymine, and coumarin undergo [2+2] cyclodimerization upon irradiation with ultraviolet (UV) light of wavelength ($\lambda$)>300 nm to form cyclobutane, which revert back to starting olefins upon irradiation with shorter wavelength of light. M. Hasegawa, Y. Suzuki, N. Kita, *Chemistry Letters* 1972, 317; A. Reiser, *Photoreactive Polymers: The Science and Technology of Resists*; Wiley-Interscience: New York, 1989; Y. Zheng, M. Micic; S. V. Mello, M. Mabrouki, F. M. Andreopoulos, V. Konka, S. M. Pham, R. M. Leblanc, *Macromolecules* 2002, 35, 5228; Y. Chen, J. L. Geh, *Polymer* 1996, 37, 4473. Chung et al. had utilized functional cinnamoyl polymers for photochemical self-healing. These polymeric networks cross-linked via cycloaddition to form cyclobutane groups, these highly strained dimers breaks preferentially upon crack propagation which can be restored by using appropriate wavelength of light. C. M. Chung, Y. S. Roh, S. Y. Cho, J. G. Kim, *Chemistry of Materials* 2004, 16, 3982. Coumarin derivatives and analogues contain β-ketoester which are well-known for their photochemical properties, undergoes a reversible photoinduced cycloaddition upon irradiation with light λ>310-355 nm forming dimers, joined by cyclobutane ring whereas the reverse photo cleavage reaction occurs at shorter λ<260 nm. N. Ramasubbu, T. N. G. Row, K. Venkatesan, V. Ramamurthy, C. N. R. Rao, *Journal of the Chemical Society Chemical Communications* 1982, 3, 178; Y. Chujo, K. Sada, T. Saegusa, *Macromolecules* 1990, 23, 2693; V. Ramamurthy, K. Venkatesan, *Chemical Reviews* 1987, 87, 433; L. H. Leenders, E. Schouteden, S. F. C. De, *Journal of Organic Chemistry* 1973, 38, 957. Coumarins are well known and used in the field of biology, medicine and polymer science. They find widespread applications as liquid crystalline polymers, photoactive surface, polymeric electroluminescence and biomaterials. Chen and co-workers synthesized a wide variety of coumarin functional polyesters, polyethers and polyurethanes and studied there reversible chain extension as well as chain scission. Y. Chen, R. T. Hong, *Journal of Polymer Science, Part A: Polymer Chemistry* 1997, 35, 2999; Y. Chen, C. S. Jean, *Journal of Applied Polymer Science* 1997, 64, 1759; Y. Chen, K. H. Chen, *Journal of Polymer Science, Part A: Polymer Chemistry* 35, 613; Y. Chen, C. S. Jean, *Journal of Applied Polymer Science* 1997, 64, 1749. Trenor and others have studied the photo-reversible reactions of polyethylene glycol functional coumarin. S. R. Trenor, T. E. Long, B. J. Love, *Macromolecular Chemistry and Physics* 2004, 205, 715. The photo reaction kinetics of coumarin functional polymers has also been extensively investigated with emphasis on the rate of formation of dimers in presence and absence of substituents in coumarin and its analogs.

Organic light emitting devices (OLED), photovoltaic (PV) and solar cells are susceptible to damage upon exposure to hot and humid environmental conditions. J. Gaume, P. Wong-Wah-Chung, A. Rivaton, S. Sandrine The'rias, J. Gardette, *RSC Advances*, 2011, 1, 1471: P. R. Elowe, M. A. Stempki, S. J. Rozeveld, M. W. DeGroot, *Chemistry of Materials* 2011, 23, 3915. This reduces the active lifetime of the devices. Rigid or flexible organic and inorganic coatings such as polymethyl methacrylate (PMMA) or PMMA-polyolefin are used to support and provide protection to the underlying semiconductor layers. K. Todd, H. Kedar, U.S. Patent Application Publication No. US 2011/0315206 A1, published Dec. 29, 2011; A. Jochen, S. Florian, International Patent Application Publication No. WO 2012/010360 A1, published Jan. 26, 2012; E. A. Gun, D. G. Theodore, S. B. Joseph, U.S. Patent Application Publication No. US 2011/086183 A1, published Apr. 14, 2011. These coatings however, may themselves be susceptible to formation of cracks or micro scratches upon prolonged exposure to unfavorable environmental conditions. These micro scratches act as stress concentrators sites which compromise moisture barrier properties. There is therefore a need for encapsulation materials that exhibit self-healing, in addition to low permeability to water and oxygen, optical transparency, and flexibility.

BRIEF SUMMARY OF EMBODIMENTS OF THE INVENTION

One embodiment is a compound (a coumarin-functionalized polyolefin) of the following formula:

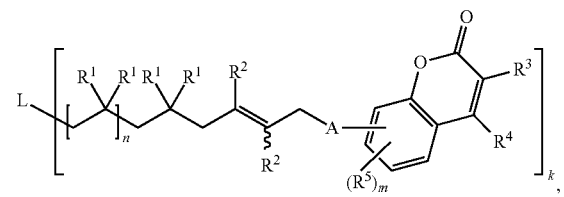

wherein L is a multivalent initiator residue; k is an integer greater than or equal to 2; A for each occurrence independently is selected from —NR$^a$—, —O—, or —OC(O)—, wherein R$^a$ is a H or a C$_1$-C$_4$ alkyl; R$^3$, R$^4$, R$^5$ for each occurrence independently is each independently selected from H, C$_1$-C$_6$ alkyl, C$_2$-C$_6$ alkenyl, amino, C$_1$-C$_6$ alkoxy, —C(O)OR$^a$, hydroxy, or a halogen; n for each occurrence independently is an integer not less than 2; m for each occurrence independently is 0, 1, 2 or 3; R$^1$ for each occurrence independently is H or a C$_1$-C$_4$ alkyl, a C$_6$ alkoxy or a substituted or unsubstituted aryl; and R$^2$ for each occurrence independently is H, X$^2$, CH$_2$X$^2$, CHX$^2_2$, CX$^2_3$, CN, or NO$_2$, wherein X$^2$, for each occurrence, is independently a halogen.

Another embodiment is a method of synthesis of the coumarin-functionalized polyolefin, comprising a step of reacting a compound represented by the following structural formula

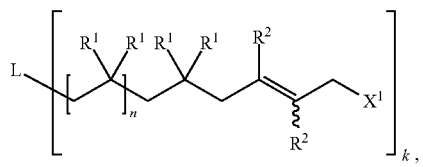

wherein X' is for each occurrence, independently, a halogen, with a compound of the following structural formula

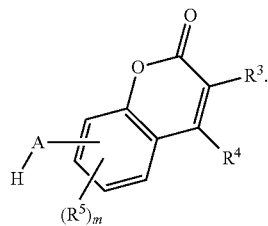

Another embodiment is a dendritic polymer including repeating unit represented by the following structure formula:

L-Y—Z$^2$—Y-L, wherein L is a multivalent initiator residue; Y, for each occurrence independently, is represented by the following structural formula

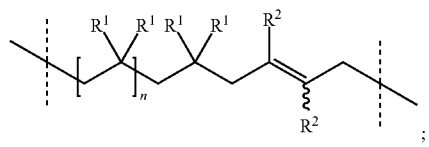

Z$^2$ is a dimer selected from

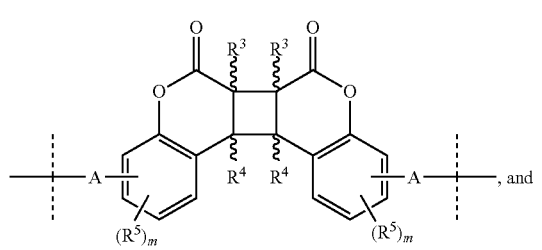

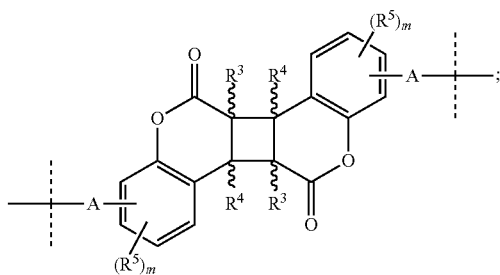

and further wherein A for each occurrence independently is selected from —NR$^a$—, —O—, or —OC(O)—, wherein R$^a$ is a H or a C$_1$-C$_4$ alkyl; R$^3$, R$^4$, R$^5$ for each occurrence independently is each independently selected from H, C$_1$-C$_6$ alkyl, C$_2$-C$_6$ alkenyl, amino, C$_1$-C$_6$ alkoxy, —C(O)OR$^a$, hydroxy, or a halogen; n for each occurrence independently is an integer not less than 2; m for each occurrence independently is 0, 1, 2 or 3; R$^1$ for each occurrence independently is H or a C$_1$-C$_4$ alkyl, a C$_1$-C$_6$ alkoxy or a substituted or unsubstituted aryl; and R$^2$ for each occurrence independently is H, X$^2$, CH$_2$X$^2$, CHX$^2_2$, CX$^2_3$, CN, or NO$_2$, wherein X$^2$, for each occurrence, is independently a halogen.

Another embodiment is a method of synthesis of a dendritic polymer, the method comprising: dimerizing a branched precursor represented by the following structural formula:

L-(Y—Z)$_k$ to produce a dendritic polymer including a repeating unit represented by the following structural formula

L-Y—Z$^2$—Y-L, wherein L is a multivalent initiator residue; k is an integer greater than or equal to 2; Y, for each occurrence independently, is represented by the following structural formula

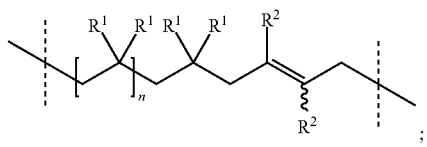

Z is represented by the following structural formula

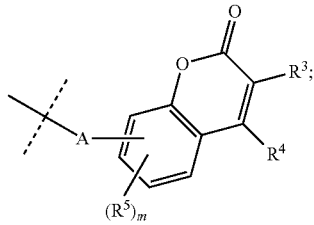

$Z^2$ is a dimer selected from

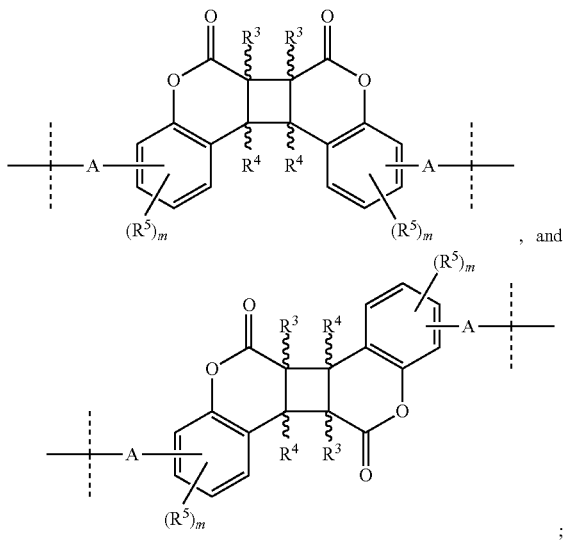

, and and further wherein A for each occurrence independently is selected from —NR$^a$—, —O—, or —OC(O)—, wherein R$^a$ is a H or a C$_1$-C$_4$ alkyl; R$^3$, R$^4$, R$^5$ for each occurrence independently is each independently selected from H, C$_1$-C$_6$ alkyl, C$_2$-C$_6$ alkenyl, amino, C$_1$-C$_6$ alkoxy, —C(O)OR$^a$, hydroxy, or a halogen; n for each occurrence independently is an integer not less than 2; m for each occurrence independently is 0, 1, 2 or 3; R$^1$ for each occurrence independently is H or a C$_1$-C$_4$ alkyl, a C$_1$-C$_6$ alkoxy or a substituted or unsubstituted aryl; and R$^2$ for each occurrence independently is H, X$^2$, CH$_2$X$^2$, CHX$^2_2$, CX$^2_3$, CN, or NO$_2$, wherein X$^2$, for each occurrence, is independently a halogen.

Another embodiment is an electronic device comprising an encapsulant or barrier layer comprising the coumarin-functionalized compound, the dendritic polymer, or a combination thereof.

These and other embodiments are described in detail below.

DETAILED DESCRIPTION OF THE INVENTION

Figure 1:
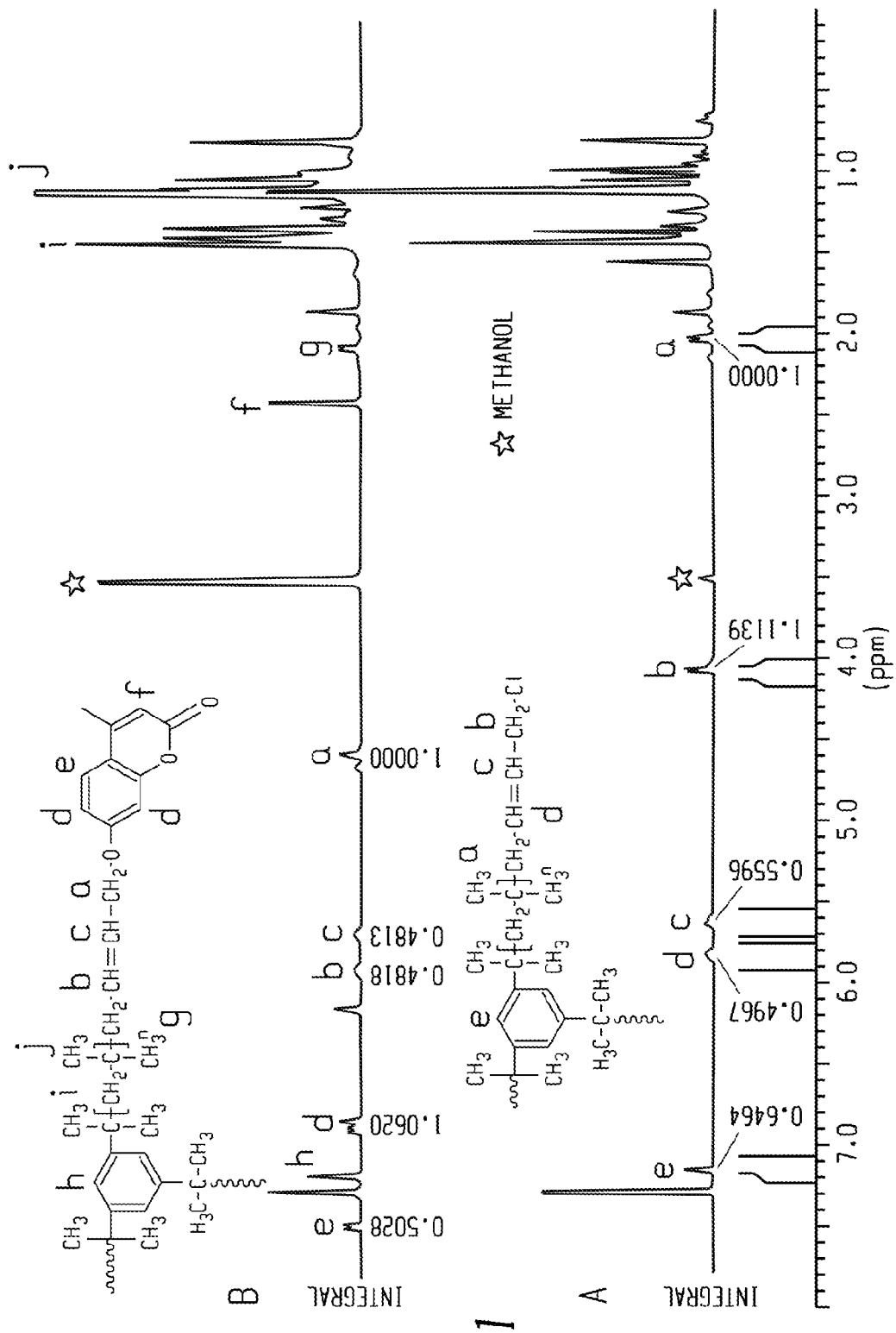
FIG. 1 consists of proton nuclear magnetic resonance ($^1$H NMR) spectra of (A) (Cl-Allyl-PIB)$_3$, and (B) (COU-PIB)$_3$. The peak marked with an asterisk is associated with methanol.

The present inventors have determined that the coumarin-functionalized polyisobutylenes described herein provide self-healing, in addition to the low permeability to the water and oxygen, optical transparency, and flexibility that are characteristic of crosslinked polyisobutylenes.

Polyisobutylene (PIB) based networks possess excellent flexibility, strong adherence to substrate, good damping and barrier properties, and thermal stability, as well as excellent chemical and solvent resistance. See, e.g., J. P. Kennedy, E. Marechal, "Carbocationic Polymerization", Wiley, New York, 1982; M. Bahadur, T. Suzuki, U.S. Pat. No. 6,069,185, 2000; J. P. Kennedy, B. Ivan, "Designed Polymers by Carbocationic Macromolecular Engineering: Theory and Practice", Hanser Publishers, Munich, 1991; G. Holden, H. R. Kricheldorf R. Quirk, Eds., "Thermoplastic Elastomers", 3rd ed.; Hanser Publishers, Munich, 2004; X. Liu, S. Rubinsztajn, U.S. Pat. No. 6,942,926, 2000; J. P. Kennedy, M. A. Sherman, U.S. Pat. No. 6,005,051, 1999; J. J. Higgins, F. C. Jagisch, N. E. Stucker, "Handbook of Adhesives, 3$^{rd}$ edition", 1990, page 185.

The properties of polyisobutylene can be effectively used for coating of electronic devices such as organic light emitting devices (OLEDs) and photovoltaic (PV) cells. The present inventors have synthesized telechelic and star macromonomers (coumarin-functionalized polyisobutylenes) in a single step SN$^2$ reaction from bromoallyl-substituted polyisobutylenes and hydroxyl-substituted coumarins in presence of a base such as sodium hydride. Quantitative conversion of end functionality is achieved. Effective polyisobutylene networks (derived from star macromonomers having three or more coumarin moieties per molecule) and chain extension (derived from "telechelic" macromonomers having two coumarin moieties per molecule) are achieved upon irradiation at a wavelength of about 310-355 nanometers. The polyisobutylene networks behave as self-healing smart coatings. The self-healing process is studied by inducing mechanical damage through micromachining with the tip of an atomic force microscope (AFM), and the rate of healing is followed by imaging of the repair process at different time intervals using AFM microscopy. UV-absorbance spectroscopy is used for characterizing the photoreactions of coumarin-end functional polyisobutylene.

As used herein, "alkyl" refers to a straight-chain or branched saturated hydrocarbon group. Examples of alkyl groups include methyl (Me), ethyl (Et), propyl (e.g., n-propyl, and isopropyl), butyl (e.g., n-butyl, isobutyl, s-butyl, t-butyl), pentyl groups (e.g., n-pentyl, isopentyl, neopentyl), and the like. A lower alkyl group typically has up to 6 carbon atoms. In various embodiments, an alkyl group has 1 to 6 carbon atoms, and is referred to as a "C 1-6 alkyl group." Examples of C 1-6 alkyl groups include, but are not limited to, methyl, ethyl, propyl (e.g., n-propyl and isopropyl), and butyl groups (e.g., n-butyl, isobutyl, s-butyl, t-butyl). A branched alkyl group has at least 3 carbon atoms (e.g., an isopropyl group) and up to 6 carbon atoms, e.g. it is a C3-6 alkyl group, i.e., a branched lower alkyl group. Examples of branched lower alkyl groups include, but are not limited to, isopropyl, isobutyl, sec-butyl, tert-butyl, isopentyl, neopentyl, and tert-pentyl. As used herein, the term "alkenyl" means a saturated straight chain or branched non-cyclic hydrocarbon having from 2 to 10 carbon atoms and having at least one carbon-carbon double bond. Representative straight chain and branched $C_2$-$C_{10}$ alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents. As used herein, the term "alkynyl" means a saturated straight chain or branched non-cyclic hydrocarbon having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. In various embodiments, a cycloalkyl group has 3-6 carbon atoms, and is referred to as a "$C_3$-$C_6$ cycloalkyl group." Examples of $C_3$-$C_6$ cycloalkyl groups include, but are not limited to, cyclopropyl, cyclopropylmethyl, cyclopropylethyl, cyclopropylpropyl, cyclobutyl, cyclobutylmethyl, cyclobutylethyl, cyclopentyl, cyclopentylmethyl, cyclohexyl, cyclopentenyl, cyclohexenyl, and cyclohexadienyl groups, as well as their homo logs, isomers, and the like. As used here, the term "alkylene" refers to a divalent alkyl group that has two points of attachment to the rest of the compound. Non-limiting examples of alkylene groups include divalent $C_1$-$C_6$ groups such as methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be optionally substituted with one or more substituents. A divalent $C_1$-$C_6$ alkyl group can be a straight chain or branched alkyl group, which as a linking group is capable of forming a covalent bond with two other moieties. Examples of a divalent $C_1$-$C_6$ alkyl group include, for example, a methylene group, an ethylene group, an ethylidene group, an n-propylene group, an isopropylene group, an isobutylene group, an s-butylene group, an n-butylene group, and a t-butylene group.

Suitable substituents for an alkyl or cycloalkyl include a halogen, an alkyl, an alkenyl, a cycloalkyl, a cycloalkenyl, an aryl, a heteroaryl, a haloalkyl, cyano, nitro, and haloalkoxy.

As used herein, "alkoxy" refers to an —O-alkyl group wherein the alkyl group may be a straight or branched chain. Examples of alkoxy groups include, but are not limited to, methoxy, ethoxy, propoxy (e.g., n-propoxy and isopropoxy), t-butoxy groups, and the like.

The term "haloalkyl", as used herein, includes an alkyl substituted with one or more F, Cl, Br, or I, wherein alkyl is defined above.

The term "aryl", as used herein, refers to a carbocyclic aromatic group. Examples of aryl groups include, but are not limited to phenyl and naphthyl. Examples of aryl groups include optionally substituted groups such as phenyl, biphenyl, naphthyl, phenanthryl, anthracenyl, pyrenyl, fluoranthyl or fluorenyl. Examples of suitable substituents on an aryl include halogen, hydroxyl, $C_1$-$C_{12}$ alkyl, $C_2$-$C_{12}$ alkene or $C_2$-$C_{12}$ alkyne, $C_3$-$C_{12}$ cycloalkyl, $C_1$-$C_{12}$ haloalkyl, $C_1$-$C_{12}$ alkoxy, aryloxy, arylamino or aryl group.

The term "aryloxy", as used herein, means an "aryl-O—" group, wherein aryl is defined above. Examples of an aryloxy group include phenoxy or naphthoxy groups.

The term "heteroaryl", as used herein, refers to aromatic groups containing one or more heteroatoms (O, S, or N). A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. The foregoing heteroaryl groups may be C-attached or N-attached (where such is possible). For instance, a group derived from pyrrole may be pyrrol-1-yl (N-attached) or pyrrol-3-yl (C-attached). Suitable substituents for heteroaryl are as defined above with respect to aryl group.

Further examples of suitable substituents for a substitutable carbon atom in an aryl, a heteroaryl, alkyl or cycloalkyl include but are not limited to —OH, halogen (—F, —Cl, —Br, and —I), —R, —OR, —$CH_2$R, —$CH_2$OR, —$CH_2CH_2$OR. Each R is independently an alkyl group. In some embodiments, suitable substituents for a substitutable carbon atom in an aryl, a heteroaryl or an aryl portion of an arylalkenyl include halogen, hydroxyl, $C_1$-$C_{12}$ alkyl, $C_2$-$C_{12}$ alkenyl or $C_2$-$C_{12}$ alkynyl group, $C_1$-$C_{12}$ alkoxy, aryloxy group, arylamino group and $C_1$-$C_{12}$ haloalkyl. In addition, aliphatic carbon atoms in the above-mentioned groups may also be substituted with =O, =S, or =N-alkyl.

As used herein, the term "amino group" may refer to a primary (—$NH_2$), secondary (—$NHR_p$), or tertiary (—$NR_pR_q$) amino, wherein $R_p$ and $R_q$ may be any of the alkyl, alkenyl, alkynyl, alkoxy, cycloalkyl, cycloalkoxy, aryl, heteroaryl, and a bicyclic carbocyclic group.

One embodiment is a coumarin-functionalized compound of the following formula:

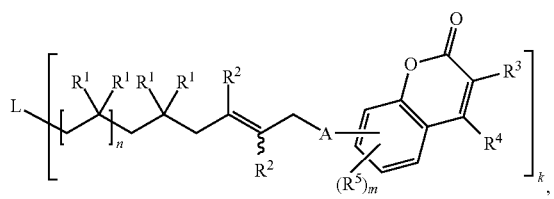

wherein L is a multivalent initiator residue; k is an integer greater than or equal to 2; A for each occurrence independently is selected from $-NR^a-$, $-O-$, or $-OC(O)-$, wherein $R^a$ is a H or a $C_1$-$C_4$ alkyl; $R^3$, $R^4$, $R^5$ for each occurrence independently is each independently selected from H, $C_1$-$C_6$ alkyl, $C_2$-$C_6$ alkenyl, amino, $C_1$-$C_6$ alkoxy, $-C(O)OR^a$, hydroxy, or a halogen; n for each occurrence independently is an integer not less than 2; m for each occurrence independently is 0, 1, 2 or 3; $R^1$ for each occurrence independently is H or a $C_1$-$C_4$ alkyl, a $C_1$-$C_6$ alkoxy or a substituted or unsubstituted aryl; and $R^2$ for each occurrence independently is H, $X^2$, $CH_2X^2$, $CHX^2{}_2$, $CX^2{}_3$, CN, or $NO_2$, wherein $X^2$, for each occurrence, is independently a halogen.

In the chemical formula above for the coumarin-functionalized compound, L is the residue of a multivalent (k-valent) initiator. The multivalent initiator includes at least two groups that are copolymerizable with alkenes such as isobutylene or are precursors to groups copolymerizable with alkenes such as isobutylene. Such functional groups can include halogens, vinyl groups, vinyloxy groups, allyl groups, allyloxy groups, (meth)acryloyl groups, cyanoacryloyl groups, and combinations thereof. Examples of specific multivalent initiators include

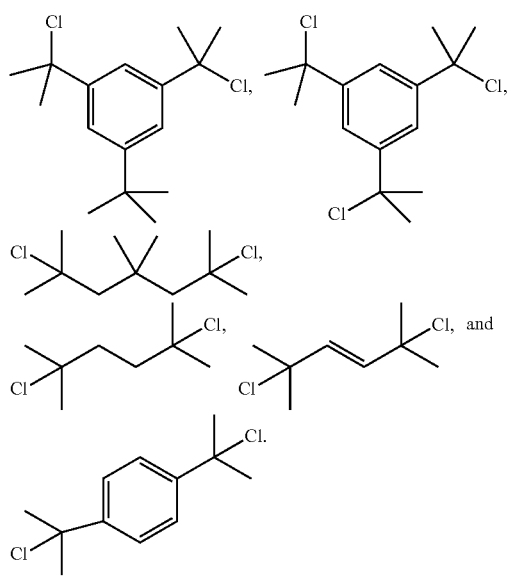

In the chemical formula above for the coumarin-functionalized compound, k is an integer greater than or equal to 2. In some embodiments, k is an integer greater than or equal to 3. In some embodiments, k is 2 to 6, specifically 3 to 6. When k is 2, then formation of a crosslinked composition requires a crosslinking agent with 3 or more coumarin moieties per molecule. When k is 3 or more, then the coumarin-functionalized compound is capable of crosslinking without added crosslinking agent. "A" is a linking group that is, independently at each occurrence, $-NR^a-$, $-O-$, or $-C(O)O-$, wherein $R^a$ is H or $C_1$-$C_4$ alkyl. In some embodiments, each occurrence of "A" is $-O-$. Each occurrence of $R^1$ is independently H, $C_1$-$C_4$ alkyl, $C_1$-$C_6$ alkoxy, or substituted or unsubstituted aryl. In some embodiments, each occurrence of $R^1$ is methyl, in which case the repeat unit

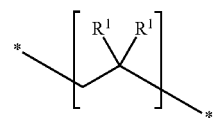

is the residue of isobutylene. Although the invention has been described using the term "polyisobutylene", it will be understood that $R^1$ is not limited to methyl, and other coumarin-functionalized polyolefins are included. Each occurrence of $R^2$ is independently H, $X^2$, $CH_2X^2$, $CHX^2{}_2$, $CX^2{}_3$, CN, or $NO_2$, wherein $X^2$, for each occurrence, is independently a halogen. In some embodiments, each occurrence of $R^2$ is H. Each occurrence of $R^3$, $R^4$, and $R^5$ is independently H, $C_1$-$C_6$ alkyl, $C_2$-$C_6$ alkenyl, amino, $C_1$-$C_6$ alkoxy, $-C(O)OR^a$, hydroxy, or halogen. In some embodiments, each occurrence of $R^3$ and $R^4$ is H. In some embodiments, each occurrence of $R^3$ is H, and each occurrence of $R^4$ is methyl. The structural variable "n" is the number average degree of polymerization (i.e., the number of repeat units). Each occurrence of "n" is an integer not less than 2. In some embodiments, each occurrence of "n" is an integer of 2 to 40, specifically 5 to 30, more specifically 10 to 30. The average value of "n" per molecule can be selected so that the coumarin-functionalized compound has a number average molecular weight of 500 to 20,000 grams/mole, specifically 500 to 10,000 grams/mole, more specifically 1,000 to 10,000 grams/mole. Each occurrence of "m" is independently is 0, 1, 2 or 3. In some embodiments, each occurrence of "m" is 0.

In some embodiments of the coumarin-functionalized compound above, each occurrence of $R^1$ is independently H or $C_1$-$C_4$ alkyl, and each occurrence of $R^2$ is H.

In some embodiments of the coumarin-functionalized compound above, each occurrence of "A" is independently is $-NR^a-$ or $-O-$, each occurrence of m is 0, and each occurrence of $R^3$ and $R^4$ is independently H, $C_1$-$C_6$ alkyl, or $-C(O)OR^a$.

In some embodiments, the coumarin-functionalized compound above is represented by the following structural formula:

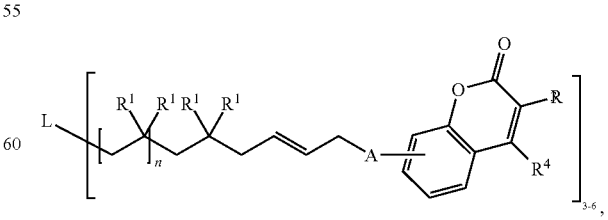

wherein L is a multivalent initiator residue; each occurrence of n is independently an integer not less than 2; each occurrence of "A" is $-NR^a-$, $-O-$, or $-C(O)O-$, wherein $R^a$ is H or $C_1$-$C_4$ alkyl; and each occurrence of $R^3$ and $R^4$ is independently H, $C_1$-$C_6$ alkyl, $C_2$-$C_6$ alkenyl, amino, $C_1$-$C_6$ alkoxy, —C(O)O$R^a$, hydroxy, or halogen.

In a very specific embodiment, the coumarin-functionalized compound is represented by the following structural formula:

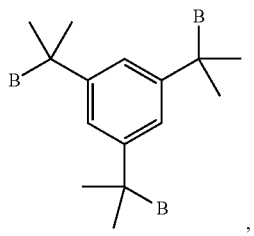

wherein

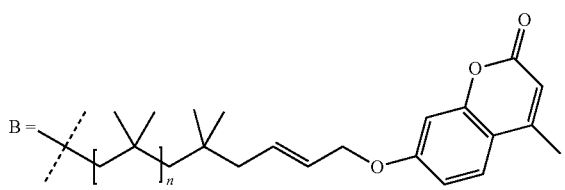

The invention includes methods of preparing the coumarin-functionalized compound. Thus, one embodiment is a method of synthesis of a compound of claim 1, comprising a step of reacting a compound represented by the following structural formula

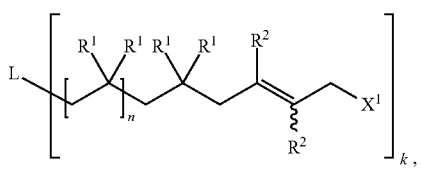

wherein L is a multivalent initiator residue; k is an integer greater than or equal to 2; n is independently at each occurrence an integer not less than 2; each occurrence of $R^1$ is independently H, $C_1$-$C_4$ alkyl, $C_1$-$C_6$ alkoxy, or substituted or unsubstituted aryl; each occurrence of $R^2$ is independently H, $X^2$, $CH_2X^2$, $CHX^2_2$, $CX^2_3$, CN, or $NO_2$, wherein $X^2$, for each occurrence, is independently a halogen; and $X^1$ is a halogen, with a compound of the following structural formula

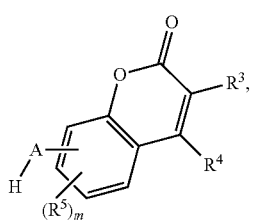

wherein A is selected from —N$R^a$—, —O—, or —OC(O)—, wherein $R^a$ is a H or a $C_1$-$C_4$ alkyl; $R^3$ and $R^4$ are independently H, $C_1$-$C_6$ alkyl, $C_2$-$C_6$ alkenyl, amino, $C_1$-$C_6$ alkoxy, —C(O)O$R^a$, hydroxy, or halogen; $R^5$ is independently at each occurrence H, $C_1$-$C_6$ alkyl, $C_2$-$C_6$ alkenyl, amino, $C_1$-$C_6$ alkoxy, —C(O)O$R^a$, hydroxy, or halogen; and m is 0, 1, 2 or 3.

All of the above-described variations in the coumarin-functionalized compound apply as well to the method of forming the coumarin-functionalized compound. In a very specific embodiment of the method, it comprises the step of reacting a compound represented by the following structural formula

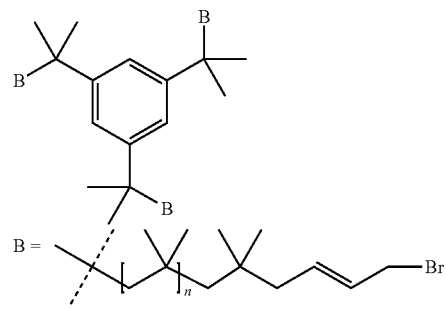

with a compound represented by the following structural formula:

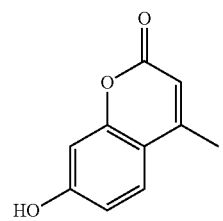

Another embodiment is a polymer formed by dimerizing the coumarin functionalities of two molecules of the coumarin-functionalized compound. If only two coumarin groups (one per molecule) are dimerized, the polymer can be described as a dimer of the coumarin-functionalized compound. If more than two coumarin groups per molecule are dimerized, the polymer can be described as crosslinked or dendritic. Thus, one embodiment is a polymer including repeating unit represented by the following structure formula:

L-Y—$Z^2$—Y-L, wherein each occurrence of L is a multivalent initiator residue; each occurrence of Y is represented by the following structural formula

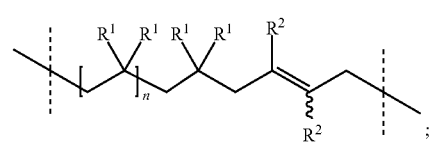

wherein each occurrence of $R^1$ is independently H, $C_1$-$C_4$ alkyl, $C_1$-$C_6$ alkoxy, or a substituted or unsubstituted aryl; each occurrence of $R^2$ is independently H, $X^2$, $CH_2X^2$, $CHX^2_2$, $CX^2_3$, CN, or $NO_2$, wherein each occurrence of $X^2$ is independently a halogen; and each occurrence of n is independently an integer not less than 2; and $Z^2$ is a dimer selected from

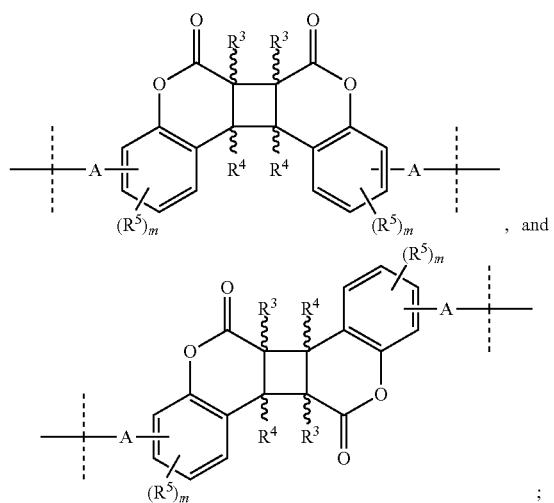

, and

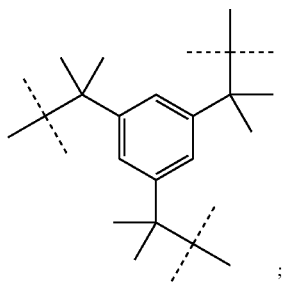

;

wherein each occurrence of A is independently —NR$^a$—, —O—, or —OC(O)—, wherein R$^a$ is a H or a $C_1$-$C_4$ alkyl; each occurrence of R$^3$, R$^4$, and R$^5$ is independently H, $C_1$-$C_6$ alkyl, $C_2$-$C_6$ alkenyl, amino, $C_1$-$C_6$ alkoxy, —C(O)OR$^a$, hydroxy, or halogen; and m for each occurrence independently is 0, 1, 2 or 3.

In a very specific embodiment of the polymer formed by dimerizing the coumarin functionalities of two molecules of the coumarin-functionalized compound, L is represented by the following structural formula:

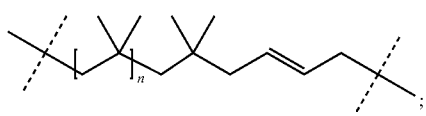

;

Y is represented by the following structural formula:

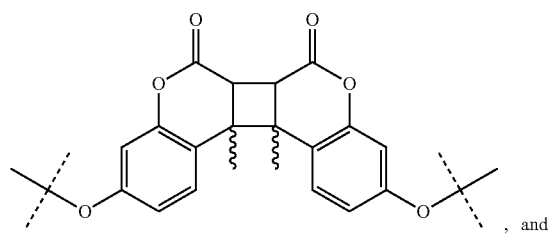

;

and
Z$^2$ is a dimer selected from

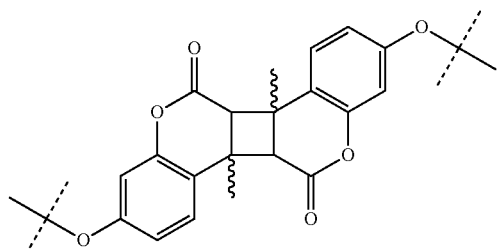

The invention includes a method of synthesizing the polymer formed by dimerizing the coumarin functionalities of two molecules of the coumarin-functionalized compound. Thus, one embodiment is a method of synthesis of a polymer, the method comprising: dimerizing a branched precursor represented by the following structural formula:

to produce a dendritic polymer including a repeating unit represented by the following structural formula:

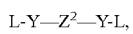

wherein L is a multivalent initiator residue; k is an integer greater than or equal to 2; each occurrence of Y is independently represented by the following structural formula

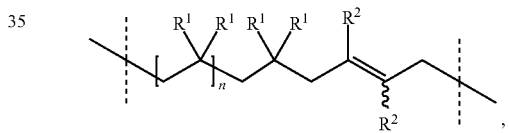

wherein each occurrence of R$^1$ is independently H, $C_1$-$C_4$ alkyl, $C_1$-$C_6$ alkoxy, or a substituted or unsubstituted aryl; each occurrence of R$^2$ is independently H, X$^2$, CH$_2$X$^2$, CHX$^2_2$, CX$^2_3$, CN, or NO$_2$, wherein each occurrence of X$^2$ is independently a halogen; and each occurrence of n is independently an integer not less than 2; wherein Z is represented by the following structural formula:

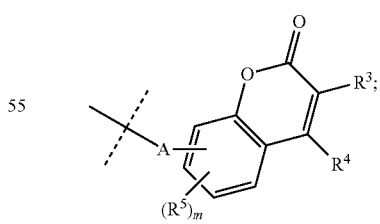

wherein each occurrence of A is independently —NR$^a$—, —O—, or —OC(O)—, wherein R$^a$ is a H or $C_1$-$C_4$ alkyl; each occurrence of R$^3$, R$^4$, and R$^5$ is independently H, $C_1$-$C_6$ alkyl, $C_2$-$C_6$ alkenyl, amino, $C_1$-$C_6$ alkoxy, —C(O)OR$^a$, hydroxy, or halogen; and m is 0, 1, 2 or 3; wherein Z$^2$ is a dimer selected from

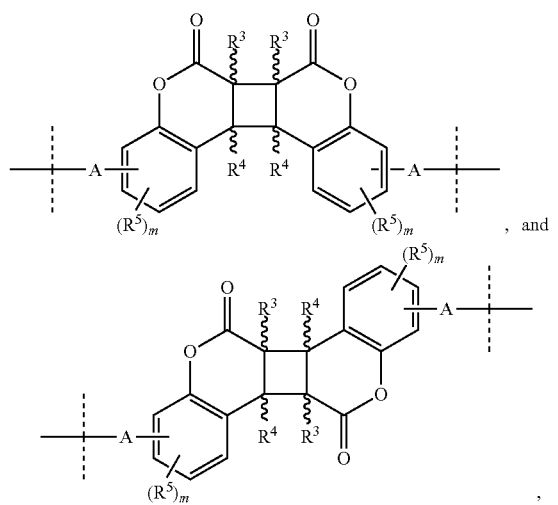

wherein A, $R^3$, $R^4$, $R^5$, and m are as defined above. Dimerizing the branched precursor can include exposing the branched precursor to the ultraviolet radiation.

In a very specific embodiment of the method of synthesis of a polymer, L is represented by the following structural formula:

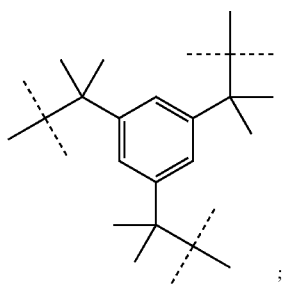

Y is represented by the following structural formula:

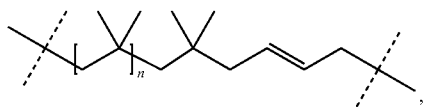

wherein each occurrence of n is independently an integer not less than 2; Z is represented by the following structural formula:

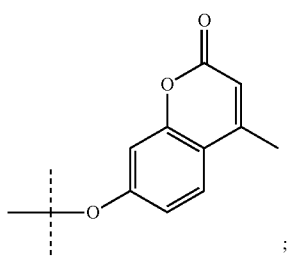

and $Z^2$ is a dimer selected from

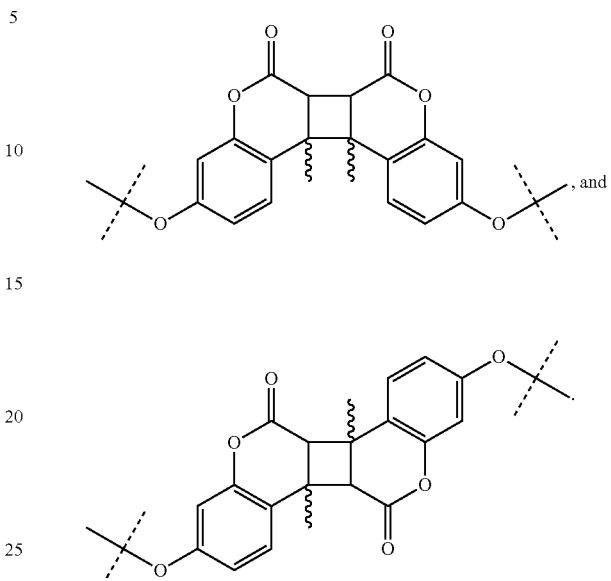

The invention includes electronic devices incorporating a layer comprising the coumarin-functionalized compound, the polymer formed by dimerizing the coumarin functionalities of the coumarin-functionalized compound, or a combination thereof. In general, the healing process starts with a scratch in the polymer formed by dimerizing the coumarin functionalities of the coumarin-functionalized compound (sometimes referred to herein as the dendritic polymer). Formation of a scratch cleaves the coumarin dimers in the area of the scratch, and irradiation with ultraviolet light having a wavelength of roughly 310 to 355 nanometers re-forms the coumarin dimers and repairs or "heals" the scratch. The electronic device can be a light emitting diode or a photovoltaic device, wherein the device comprises an encapsulating layer comprising the coumarin-functionalized compound, the polymer formed by dimerizing the coumarin functionalities of the coumarin-functionalized compound, or a combination thereof. The structures of electronic devices comprising encapsulating layers of other materials are known. See, e.g., J. Gaume, P. Wong-Wah-Chung, A. Rivaton, S. Sandrine The'rias, J. Gardette, *RSC Advances*, 2011, 1, 1471 (describing a solar cell with a poly(vinyl alcohol) oxygen barrier layer); P. R. Elowe, M. A. Stempki, S. J. Rozeveld, M. W. DeGroot, *Chemistry of Materials* 2011, 23, 3915 (describing solar cells with tantalum nitride/silicon nitride bilayer barrier thin films); A. Jochen, S. Florian, International Patent Application Publication No. WO 2012/010360 A1 (describing photovoltaic systems with barrier layers formed from poly(methyl methacrylate) or poly(methyl methacrylate)-polyolefin coextrudate). The coumarin-functionalized compound, the polymer formed by dimerizing the coumarin functionalities of the coumarin-functionalized compound, or a combination

17 thereof can be substituted for the materials of prior art encapsulating layers.

The invention includes at least the following embodiments.

Embodiment 1

A compound of the following formula:

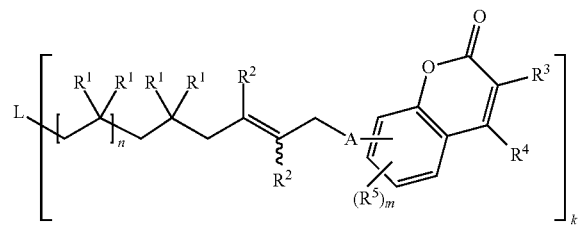

wherein L is a multivalent initiator residue; k is an integer greater than or equal to 2; A for each occurrence independently is selected from —NR$^a$—, —O—, or —OC(O)—, wherein R$^a$ is a H or a C$_1$-C$_4$ alkyl; R$^3$, R$^4$, R$^5$ for each occurrence independently is each independently selected from H, C$_1$-C$_6$ alkyl, C$_2$-C$_6$ alkenyl, amino, C$_1$-C$_6$ alkoxy, —C(O)OR$^a$, hydroxy, or a halogen; n for each occurrence independently is an integer not less than 2; m for each occurrence independently is 0, 1, 2 or 3; R$^1$ for each occurrence independently is H or a C$_1$-C$_4$ alkyl, a C$_1$-C$_6$ alkoxy or a substituted or unsubstituted aryl; and R$^2$ for each occurrence independently is H, X$^2$, CH$_2$X$^2$, CHX$^2_2$, CX$^2_3$, CN, or NO$_2$, wherein X$^2$, for each occurrence, is independently a halogen.

Embodiment 2

The compound of Embodiment 1, wherein R$^1$ for each occasion is independently H or a C$_1$-C$_4$ alkyl; and R$^2$ for each occasion is independently H.

Embodiment 3

The compound of Embodiment 1 or 2, wherein A for each occurrence independently is selected from —NR$^a$— or —O—; m is 0; and R$^3$ and R$^4$ is each independently selected from H, C$_1$-C$_6$ alkyl, or —C(O)OR$^a$.

Embodiment 4

The compound of Embodiment 1, represented by the following structural formula:

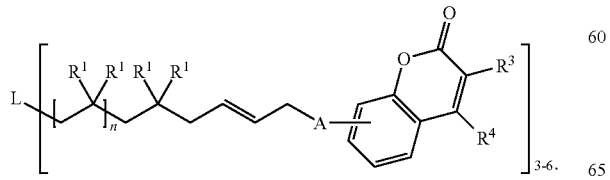

18

Embodiment 5

The compound of Embodiment 1, represented by the following structural formula:

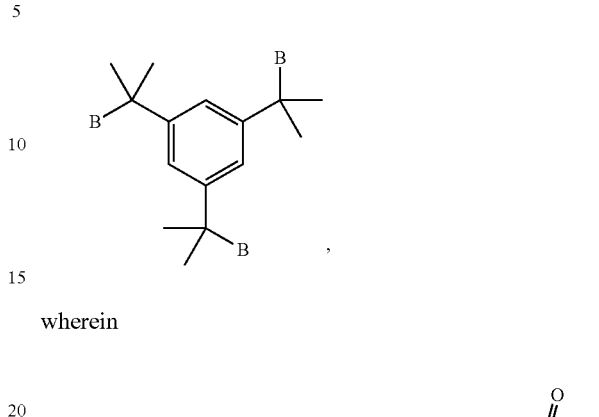

wherein

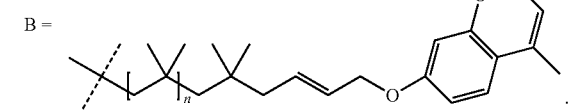

Embodiment 6

A method of synthesis of a compound of Embodiment 1, comprising a step of reacting a compound represented by the following structural formula

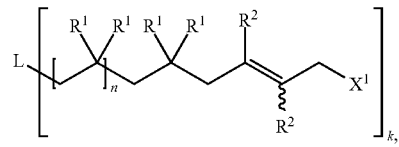

wherein X$^1$ is for each occurrence, independently, a halogen, with a compound of the following structural formula

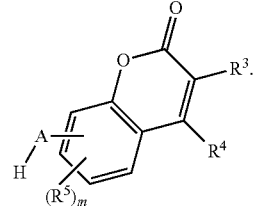

Embodiment 7

The method of Embodiment 6, comprising the step of reacting the compound represented by the following structural formula

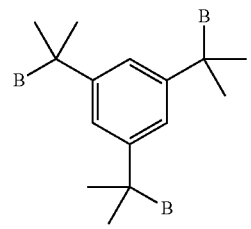

B = 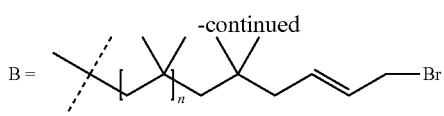

with the compound represented by the following structural formula:

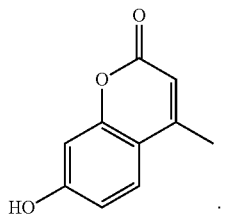

Embodiment 8

A dendritic polymer including repeating unit represented by the following structure formula:

$$L\text{-}Y\text{-}Z^2\text{-}Y\text{-}L,$$

wherein L is a multivalent initiator residue; Y, for each occurrence independently, is represented by the following structural formula

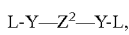

$Z^2$ is a dimer selected from

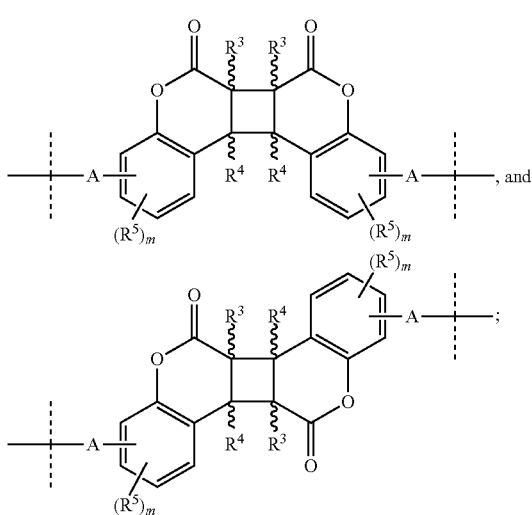

and further wherein A for each occurrence independently is selected from $-NR^a-$, $-O-$, or $-OC(O)-$, wherein $R^a$ is a H or a $C_1$-$C_4$ alkyl; $R^3$, $R^4$, $R^5$ for each occurrence independently is each selected from H, $C_1$-$C_6$ alkyl, $C_2$-$C_6$ alkenyl, amino, $C_1$-$C_6$ alkoxy, $-C(O)OR^a$, hydroxy, or a halogen; n for each occurrence independently is an integer not less than 2; m for each occurrence independently is 0, 1, 2 or 3; $R^1$ for each occurrence independently is H or a $C_1$-$C_4$ alkyl, a $C_1$-$C_6$ alkoxy or a substituted or unsubstituted aryl; and $R^2$ for each occurrence independently is H, $X^2$, $CH_2X^2$, $CHX^2_2$, $CX^2_3$, CN, or $NO_2$, wherein $X^2$, for each occurrence, is independently a halogen.

Embodiment 9

The dendritic polymer of Embodiment 8, wherein: L is represented by the following structural formula:

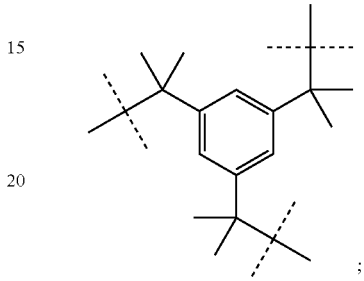

Y is represented by the following structural formula:

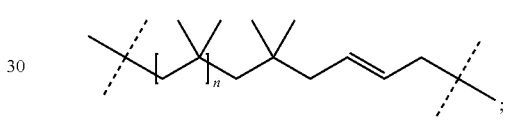

and
$Z^2$ is a dimer selected from

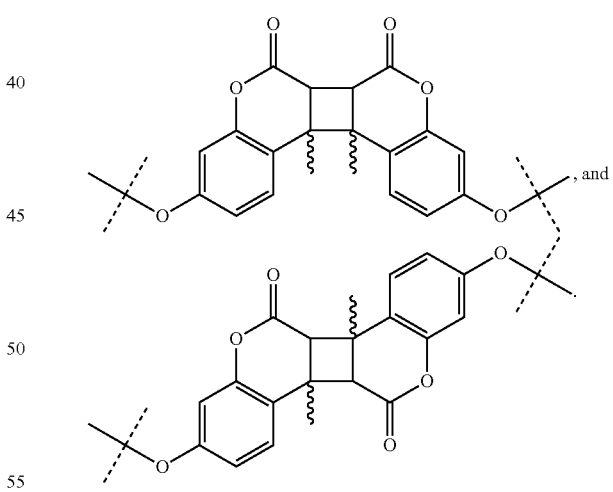

Embodiment 10

A method of synthesis of a dendritic polymer, the method comprising: dimerizing a branched precursor represented by the following structural formula:

$$L\text{-}(Y\text{-}Z)_k$$

to produce a dendritic polymer including a repeating unit represented by the following structural formula:

$$L\text{-}Y\text{-}Z^2\text{-}Y\text{-}L,$$

wherein L is a multivalent initiator residue; k is an integer greater than or equal to 2; Y, for each occurrence independently, is represented by the following structural formula

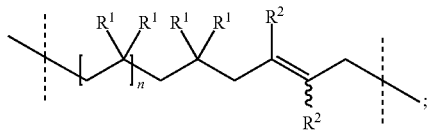

Z is represented by the following structural formula:

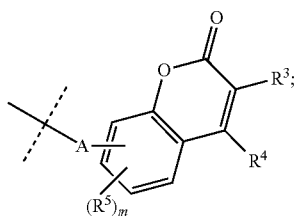

$Z^2$ is a dimer selected from

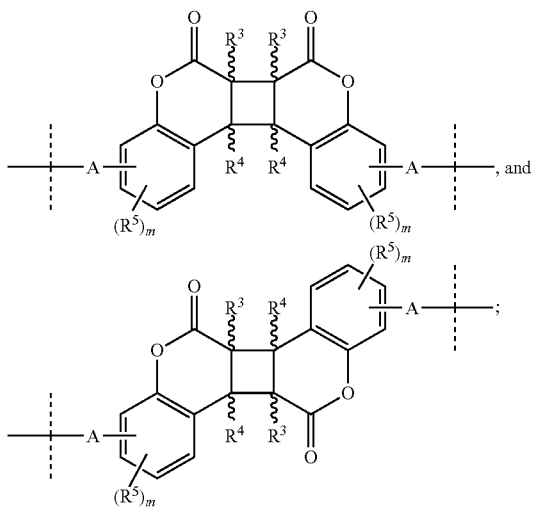

and further wherein A for each occurrence independently is selected from —NR$^a$—, —O—, or —OC(O)—, wherein R$^a$ is a H or a $C_1$-$C_4$ alkyl; R$^3$, R$^4$, R$^5$ for each occurrence independently is each independently selected from H, $C_1$-$C_6$ alkyl, $C_2$-$C_6$ alkenyl, amino, $C_1$-$C_6$ alkoxy, —C(O)OR$^a$, hydroxy, or a halogen; n for each occurrence independently is an integer not less than 2; m for each occurrence independently is 0, 1, 2 or 3; R$^1$ for each occurrence independently is H or a $C_1$-$C_4$ alkyl, a $C_1$-$C_6$ alkoxy or a substituted or unsubstituted aryl; and R$^2$ for each occurrence independently is H, $X^2$, $CH_2X^2$, $CHX^2_2$, $CX^2_3$, CN, or $NO_2$, wherein $X^2$, for each occurrence, is independently a halogen.

Embodiment 11

The method of Embodiment 10, wherein dimerizing the branched precursor includes exposing the branched precursor to the ultraviolet radiation.

Embodiment 12

The method of Embodiment 10, wherein L is represented by the following structural formula:

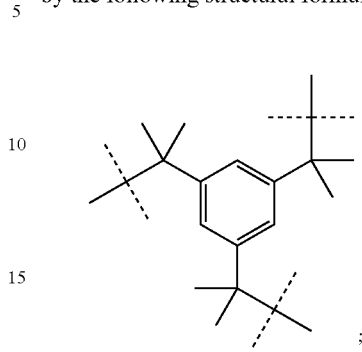

Y is represented by the following structural formula:

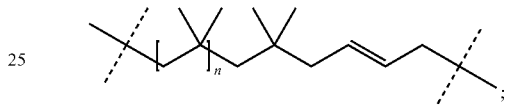

Z is represented by the following structural formula:

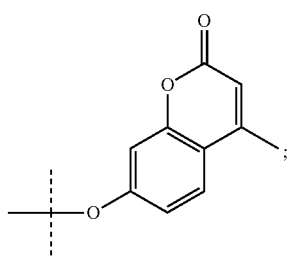

and
$Z^2$ is a dimer selected from

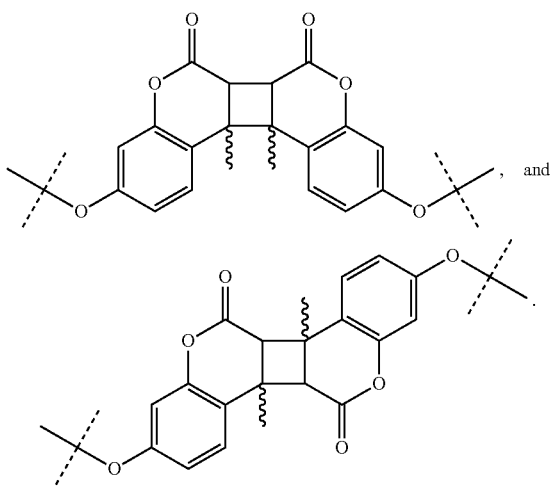

Embodiment 13

An electronic device comprising an encapsulant or barrier layer comprising the compound of any of embodiments 1-5, the dendritic polymer of any of embodiments 8 and 9, or a combination thereof.

Embodiment 14

The electronic device of embodiment 13, selected from a light emitting diode and a photovoltaic device.

All ranges disclosed herein are inclusive of the endpoints, and the endpoints are independently combinable with each other. Each range disclosed herein constitutes a disclosure of any point or sub-range lying within the disclosed range.

The invention is further illustrated by the following non-limiting examples.

EXAMPLES

Materials. 4-Methylumbelliferone (Aldrich, 98%), sodium hydride (NaH, Aldrich, 60% dispersion in mineral oil), potassium hydroxide (KOH, Aldrich), sodium sulfate ($Na_2SO_4$, Aldrich), were used as received. Tetra-n-butylammonium bromide (TBAB, 95%) purchased from Alfa-Aesar was used without further purification. Hexanes (Hex, Doe & Ingals, Technical grade) and methanol (Doe & Ingals, Technical grade) were purified by refluxing over sulfuric acid for 24 hours. They were washed with an aqueous solution of KOH three times followed by washing with distilled water. Then they were stored over sodium sulfate overnight at room temperature. Finally, they were distilled over $CaH_2$ under a nitrogen atmosphere before use. Tetrahydrofuran (THF, Aldrich, 99%) was refluxed over sodium metal and benzophenone overnight and distilled under a nitrogen atmosphere prior to use. In a typical purification procedure, the polymer (~200 milligrams) was dissolved in 2 milliliters of hexanes. The solution was added to 10 milliliters of methanol and kept undisturbed until the entire polymer settled down. The supernatant liquid was slowly decanted, and the same procedure was repeated with the precipitate three times. Finally, the precipitate was dried under vacuum at room temperature for 12 hours.

Structural analysis was carried out using $^1H$ and $^{13}C$ NMR spectroscopy on a Bruker 500 MHz spectrometer using $CDCl_3$ (Cambridge Isotope laboratories, Inc.) as a solvent. Tetramethylsilane (TMS) was used as an internal standard.

Molecular weights were measured with a Waters HPLC system equipped with a model 515 HPLC pump, model 2410 differential refractometer, model 2487 absorbance detector, online multiangle laser light scattering (MALLS) detector (MiniDawn, Wyatt Technology Inc.), on-line differential viscometer (ViscoStar, Wyatt Technology Inc.), Model 717 plus sample processor, and five Styragel HR Gel Permeation Chromatography (GPC) columns connected in the following series: 500, 103, 104, 105, and 100 Å. THF was used as an eluent at a flow rate of 1 mL/min. The molecular weight was calculated using Universal Calibration curve (UCAL). The UCAL curve was constructed by injecting a series of narrow polystyrene standards of known molecular weight.

A 2 weight percent solution of coumarin-functionalized polyisobutylene (COU-PIB) was made in tetrahydrofuran by dissolving 20 milligrams of the polymer in 1 milliliter of the solvent. The solution was filtered through 0.45 micrometer pore size filter paper to obtain a clear homogeneous solution. Five to eight drops of the polymer solution were placed on a clean glass slide and the solvent was allowed to evaporate at room temperature. The glass slide was dried under vacuum at room temperature in dark for 2 hours to remove traces of solvent prior to use. The photodimerization reaction of polymer films was carried out at room temperature by irradiation of a 400 Watt high-pressure mercury lamp (Uvitron International Inc. PORTA-RAY 400 R) at the wavelength of 315-400 nanometers. The photocleavage was accomplished by irradiation at 254 nanometers (UV C irradiation) using a 400 Watt medium pressure visible lamp from Uvitron International Inc. The samples were placed at a distance of 15 centimeters below the lamp. The intensity of UV A irradiation on the sample was determined to be 21 milliWatts/centimeter, whereas, the measured intensity of UV C irradiation was 7.5 milliWatt/centimeter$^2$. The curing kinetics of the polymer were studied using an Agilent 8453 photodiode array UV-visible spectrophotometer. Thin films of each polymer were cast on a clean glass slide. After evaporation of the solvent, the films were exposed to UV light, wavelength, $\lambda > 315$ nanometers, and periodically the UV-visible spectrum of the film was recorded to study the extent of curing by characterization of the coumarin group.

Atomic Force Microscopy (AFM) was used to scratch the surface of spin coated samples of COU-PIB, then subsequently image the marred surfaces and monitor the progression of healing. A Veeco Nanoscope IIIa Multimode AFM was mounted with a rigid Veeco (TESP) Si tip with nominal spring constant, k~42 Newtons/meter, and resonant frequency, $f_0$~320 kiloHertz, and a scratch was made in the surface of the polymer film. By adjusting the deflection set point in the Nanoscope software, the tip was pushed into the film with some positive pressure, and scanned along the x-axis only, resulting in scratches with depths ranging from hundreds of nanometers to micrometers.

The scratched (COU-PIB)$_3$ samples were irradiated with 400 Watt medium pressure visible lamp or low power UV light (0.3 milliWatt/centimeter$^2$) at 254 and 365 nanometers, as well as a control sample which was protected from light. At time zero, and after various irradiation times, images of the scratch area were obtained at ambient conditions and room temperature using contact mode AFM. A Veeco (DNP-S10) $SiNi_3$ tip with k~0.35 Newton/meter, and $f_0$~65 kiloHertz was used for imaging. Cross sectional images and depth profiles were obtained using the Nanoscope software in Section analysis mode.

Synthesis of Coumarin-trifunctionalized polyisobutylene ((COU)-PIB)$_3$. Bromoallyl triarm PIB (number average molecular weight ($M_n$)=2010, polydispersity index (PDI)=1.15, 200 milligrams, 0.09 millimoles; prepared according to R. Faust et al. International Patent Application Publication No. WO 2010/111280 A1) was dissolved in dry tetrahydrofuran (10 milliliters) and was added into a two necked glass reactor followed by the addition of 4-methylumbelliferone (792 milligrams, 4.5 millimoles), TBAB (1.92 grams, 5.9 millimoles), and NaH (108 milligrams, 2.7 millimoles); the mixture was refluxed under a dry nitrogen atmosphere for 12 hours. The reaction mixture was cooled to room temperature, and THF was evaporated using a rotary vacuum evaporator. The residue was dissolved in hexanes, the solution was filtered, and the filtrate (polymer solution) was precipitated in methanol. The polymer was allowed to settle down. The supernatant liquid was decanted, and the sticky mass was dried under vacuum at room temperature for 12 hours. Gravimetric yield: 98%. $^1H$ NMR ($CDCl_3$, ppm, δ): 4.6 (d, 2H, —CHCH$_2$O—), 5.75 (m, 1H, —CHCHCH$_2$O—), 5.95 (m, 1H, —CHCHCH$_2$O—), 2.4 (s, 1H, —OCOCH—), 7.5 (d, 1H, ArH) and 6.9 (m, 2H, —ArH). $^{13}C$ NMR (CDCl3, ppm, δ).

Results and Discussion

Figure 2:
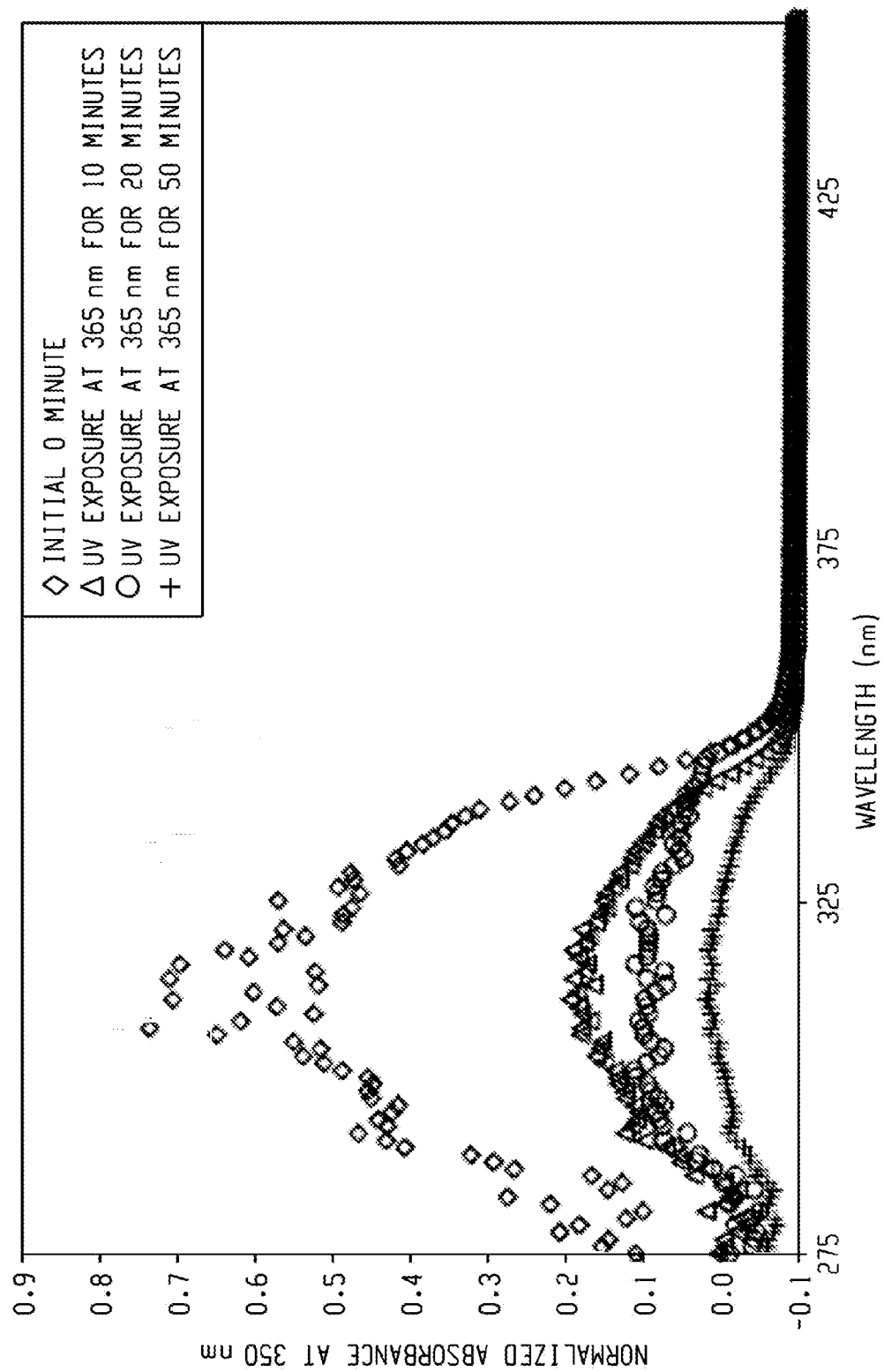
FIG. 2 consists of UV-visible spectra of (COU-PIB)$_3$ in tetrahydrofuran as a function of time of UV exposure at 365 nanometers.
Figure 3A:
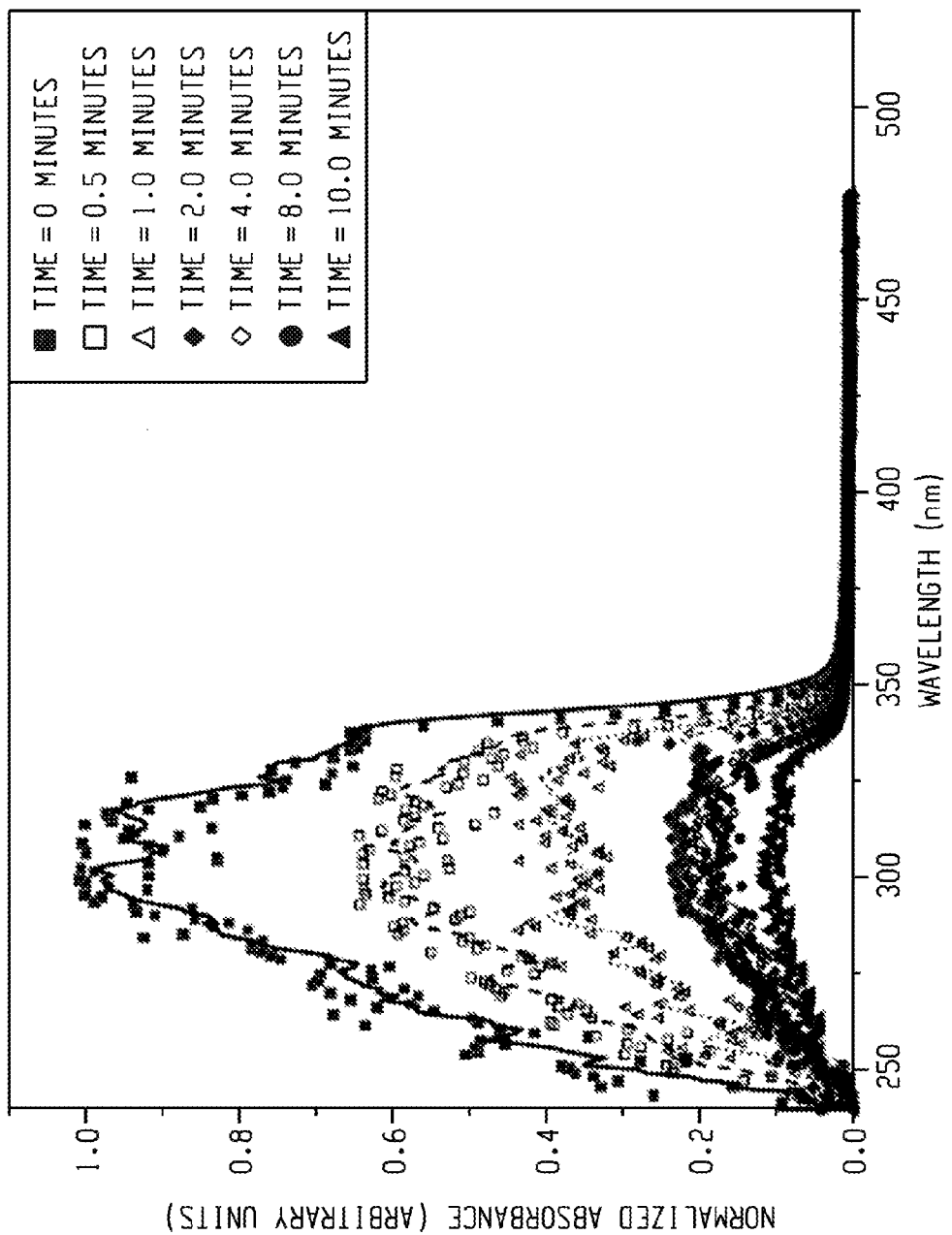
FIG. 3 consists of (a) UV-visible spectra of (COU-PIB)$_2$ in a solution cast film; and (b) degree of crosslinking of (COU-PIB)$_2$ as a function of irradiation time.
Figure 3B:
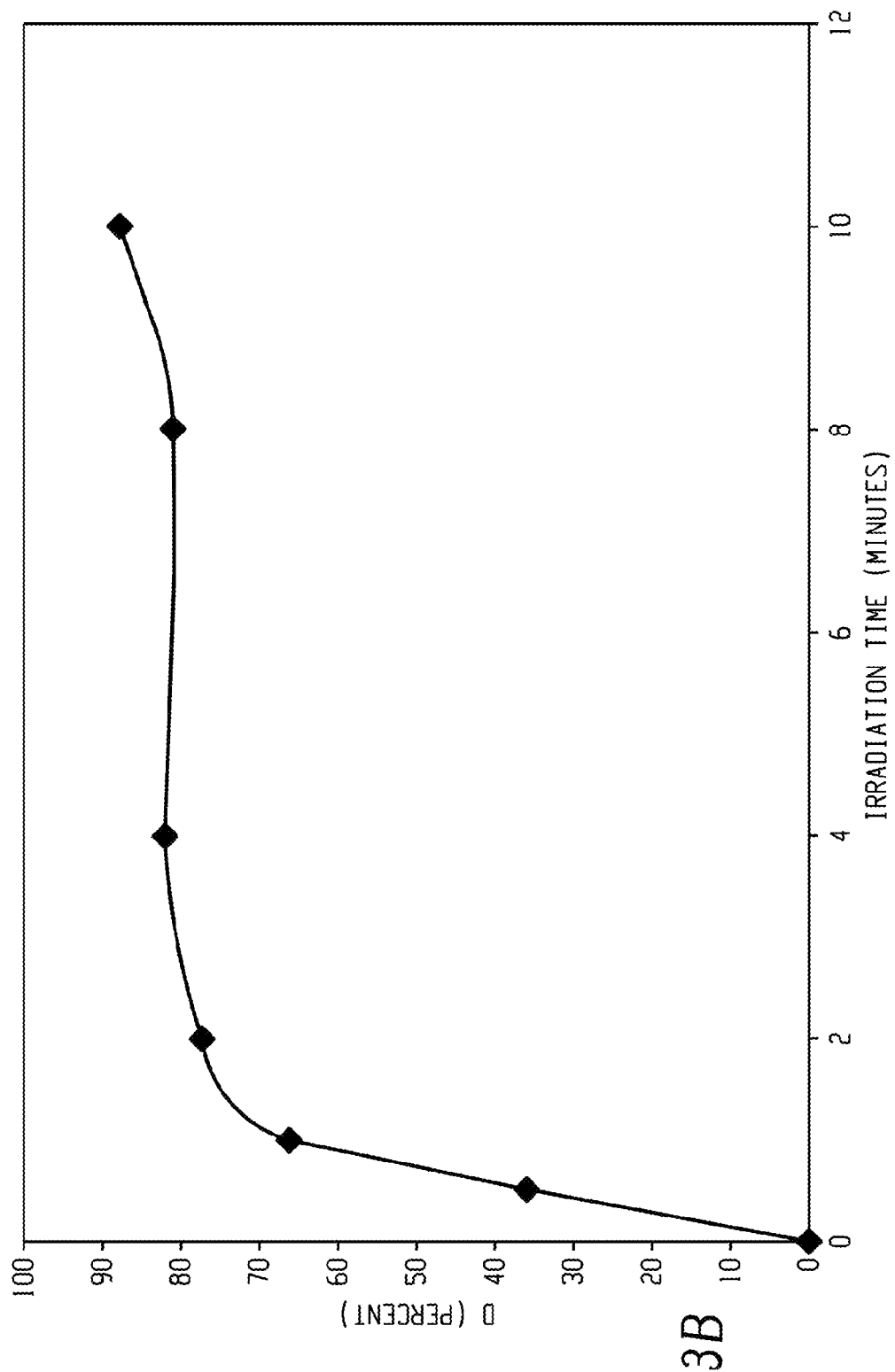
Figure 4A:
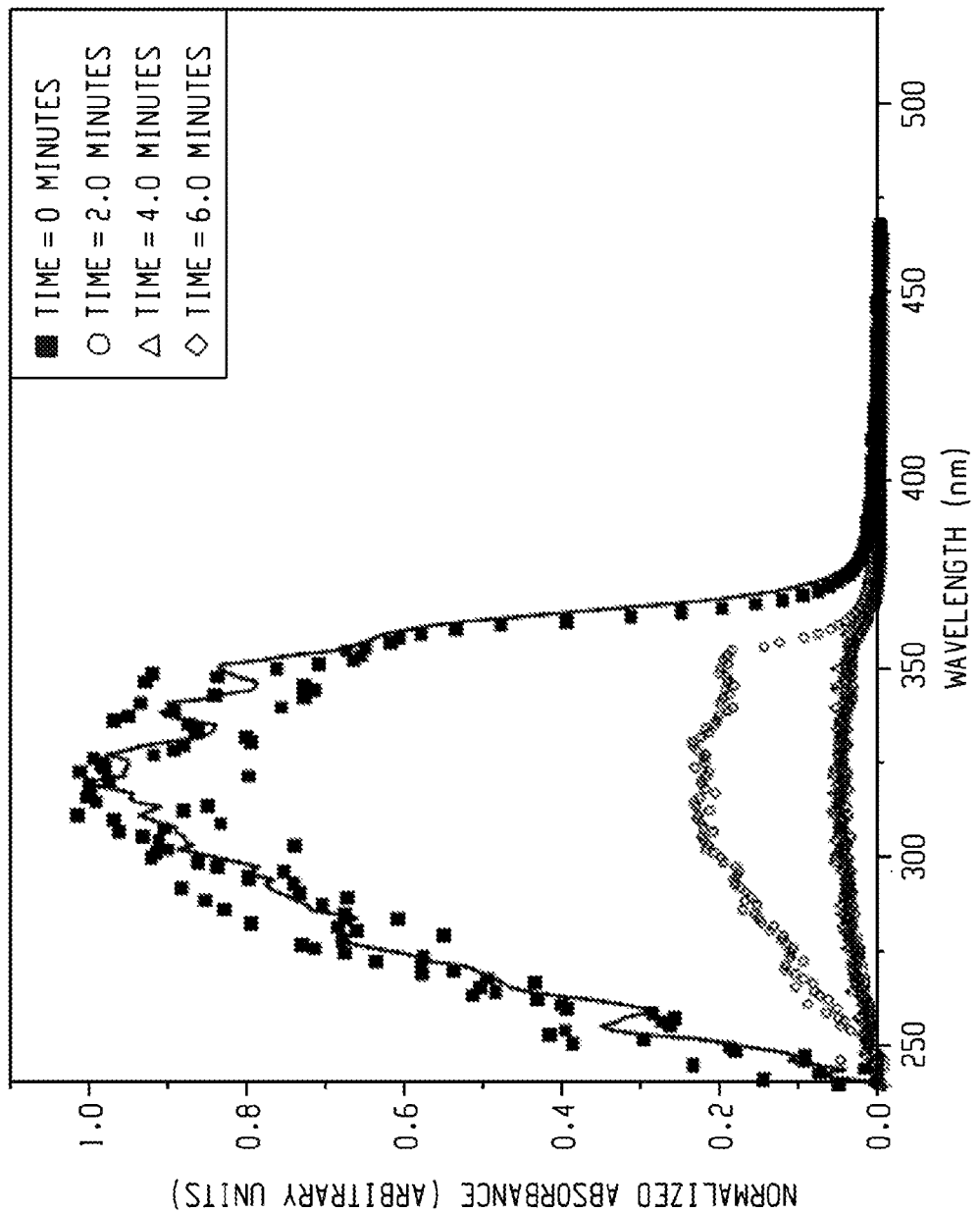
FIG. 4 consists of (a) UV-visible spectra of (COU-PIB)$_3$ in a solution cast film; and (b) degree of crosslinking of (COU-PIB)$_3$ as a function of irradiation time.
Figure 4B:
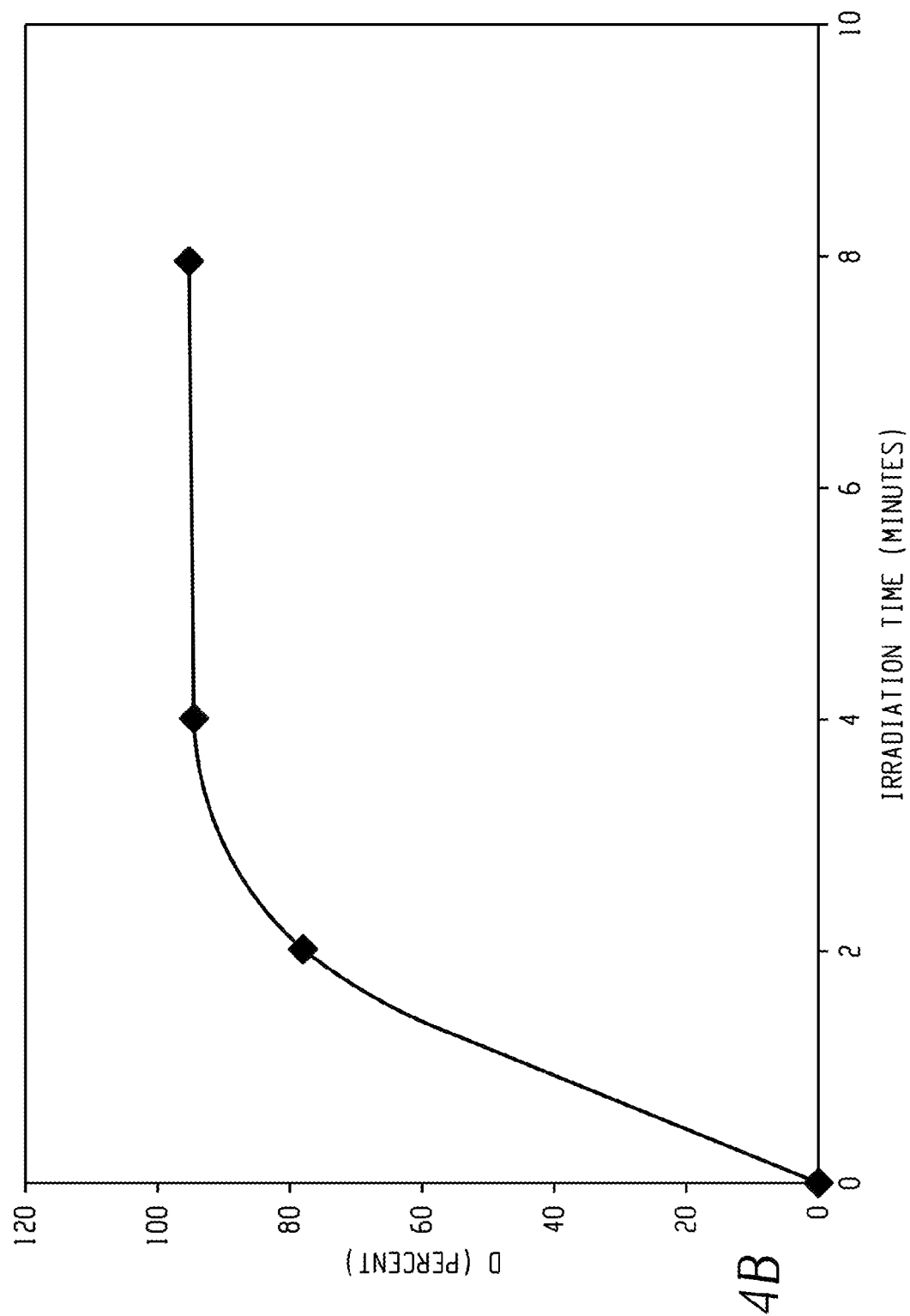

Synthesis of (COU-PIB)$_3$: The synthetic route to (COU-PIB)$_3$ is represented in Scheme 1. The macromonomers were characterized by GPC, $^1$H and $^{13}$C NMR spectroscopy techniques. 4-Methylumbelliferone was added to the bromoallyl triarm star PIB in presence of NaH to obtain the corresponding coumarin end-functional PIB. $^1$H NMR spectroscopy showed the disappearance of peaks at 4.0, 5.7, and 5.75 ppm assigned to the bromomethylene and bromoallylmethine protons and new signals at 4.6, 5.75, and 5.95 ppm assigned to —CHCH$_2$O—, —CHCHCH$_2$O— and —CHCHCH$_2$O—, indicating quantitative conversion (FIG. 1b). New peaks at 2.4, 6.9, and 7.5 ppm appeared for —OCOCH— and for aromatic protons, suggesting quantitative conversion. In the $^{13}$C NMR spectrum the characteristic signals at 64, 131 and 129 ppm assigned to —CH$_2$O, —CHCHCH$_2$O and —CHCHCH$_2$O respectively indicated complete functionalization reactions. The methylene group of the coumarin showed resonance at 19.4 ppm proved quantitative functionalization. The new signals at 154 and 160 ppm also appeared for —COC and —OCO (FIG. 1). Well defined telechelic COU-PIB of 2000 and 8000 grams/mole was synthesized using the similar synthetic procedure as described before. The GPC-RI traces of the macromonomers are identical showing no change in the polymer backbone during post functionalization reactions (FIG. 2).

coumarin groups. The coumarin chromophores are known to undergo only [2+2] photodimerizations because of its fused ring structure. As the coumarin dimerizes, the level of unsaturation decreases due to the formation of cross-links of the coumarin chromophores as result of UV light photodimerizations. Therefore the decrease in absorbance at 320 nm can be primarily attributed to the loss of coumarin chromophores as a result of [2+2] photodimerizations. The change in absorbance at 320 nm ($A_{320}$) values directly reflects the degree of cross-linking of polymers, hence the cross-linking density of polymer can be approximately estimated from the $A_{320}$ value using the following equation.

$$D=(A_{320})_0-(A_{320})_t/(A_{320})_0$$

wherein D is the degree of cross-linking, $(A_{320})_0$ and $(A_{320})_t$ are the absorbance of polymers at 320 nm before and after irradiation for t min respectively. FIG. 3(b) is a plot of the degree of crosslinking as a function of irradiation time. This plot shows that the maximum crosslinking/chain extension is achieved after about 8 minutes and then levels off. Similarly, FIG. 4 plots the dependence of the normalized absorbance and D values of tri-arm star (COU-PIB)$_3$ as a function of UV irradiation time t. In this plot, the absorbance levels off after irradiation for about 4 to 8 minutes, indicating that the photodimerization reaction seems to become more and more slow and difficult after irradiation for about 4 min. Comparing the Scheme 1

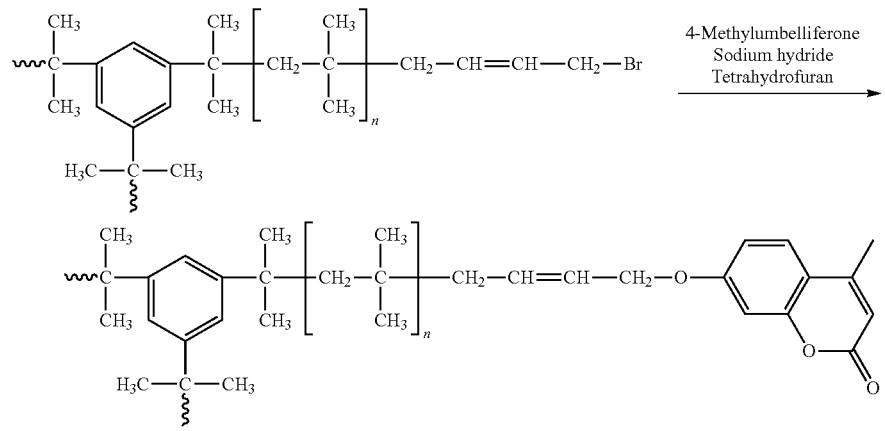

The UV-visible spectrum of the macromonomer in THF is shown in FIG. 2. The macromonomer shows the main absorption at 320 nanometers which is attributed to the maximum absorption of coumarin moieties suggesting incorporation of coumarin moiety into the PIB precursor. A low intensity UV source of 0.3 milliWatts/centimeter$^2$ of light intensity was used for irradiation of 2 weight percent of (COU-PIB)$_3$ in THF.

Photodimerization/photocleavage of COU-PIB: Coumarin and its derivatives can undergo reversible photodimerization and photoscission reactions when irradiated at different UV wavelength. The photodimerization of (COU-PIB)$_3$ of 2000 grams/mole was successfully performed through the chain extension/crosslinking of coumarin with a high pressure Hg lamp. As shown in FIG. 3(a), before irradiation of UVA light, the polymer exhibits a main absorption peak at 320 nanometers from the maximum absorption of coumarin moieties. Its absorbance at 320 nanometers significantly decreases with photoirradiation time t, resulting from the dimerization of the UV-visible spectra for the (COU-PIB)$_2$ with that of (COU-PIB)$_3$ of similar molecular weight suggests that both the macromonomers exhibit a similar trend with photoirradiation, but for (COU-PIB)$_2$, the absorbance at 320 nanometers decreases more slowly than that of (COU-PIB)$_3$. This can be explained by the fact that the rate of photodimerization depends upon the amount of coumarin attached to polymer main chain. In other words, the higher the coumarin content the faster the rate of photodimerization and higher the crosslinking density of the coumarin polymers.

Figure 5A:
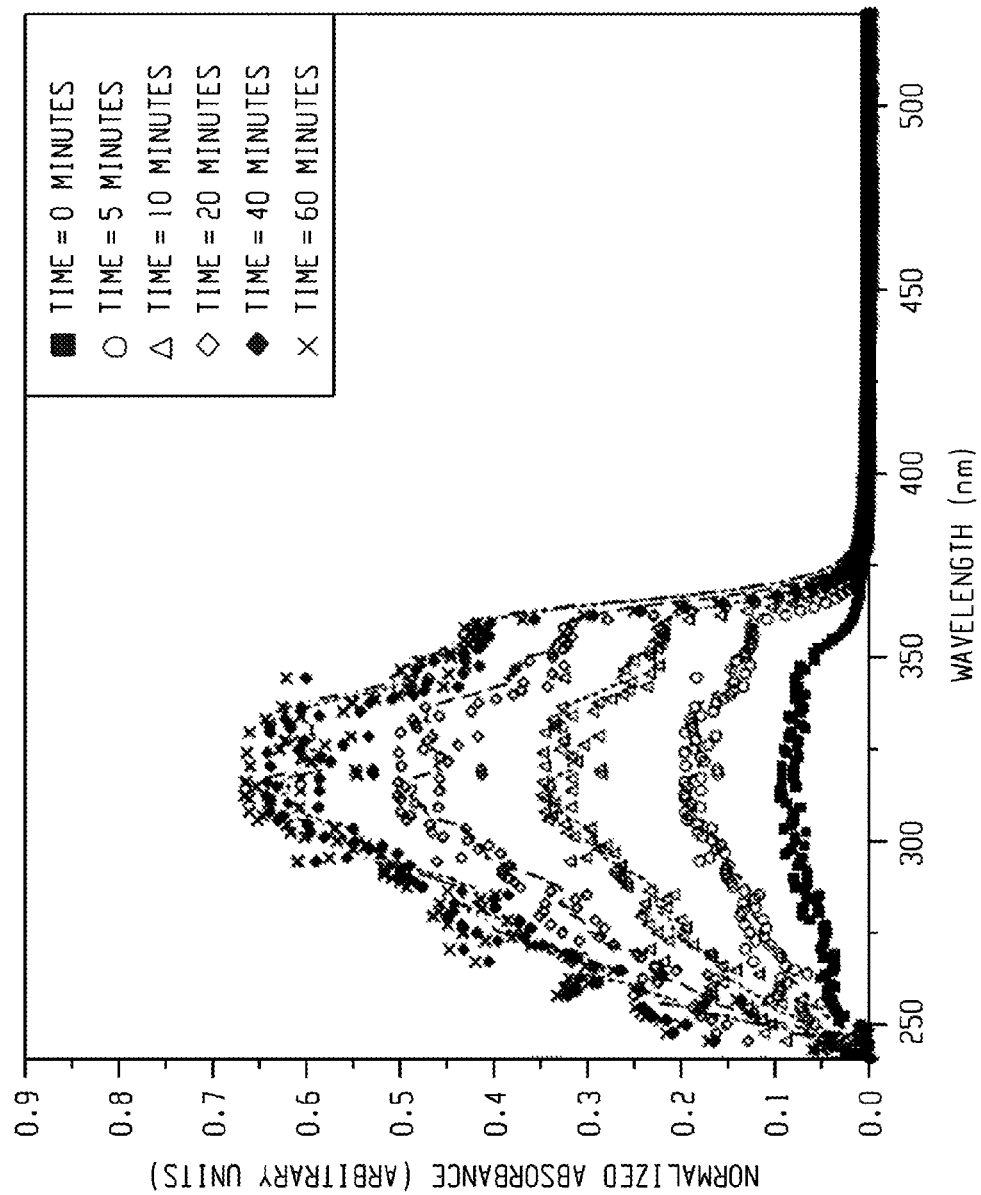
FIG. 5 consists of (a) UV-visible spectra of (COU-PIB)$_2$ as a function of irradiation time with a medium pressure broad spectrum lamp (including 254 nanometer radiation); (b) UV-visible spectra of (COU-PIB)$_3$ as a function of irradiation time with the medium pressure broad spectrum lamp. Photocleavage of the coumarin dimers occurs at wavelengths less than about 260 nanometers.
Figure 5B:
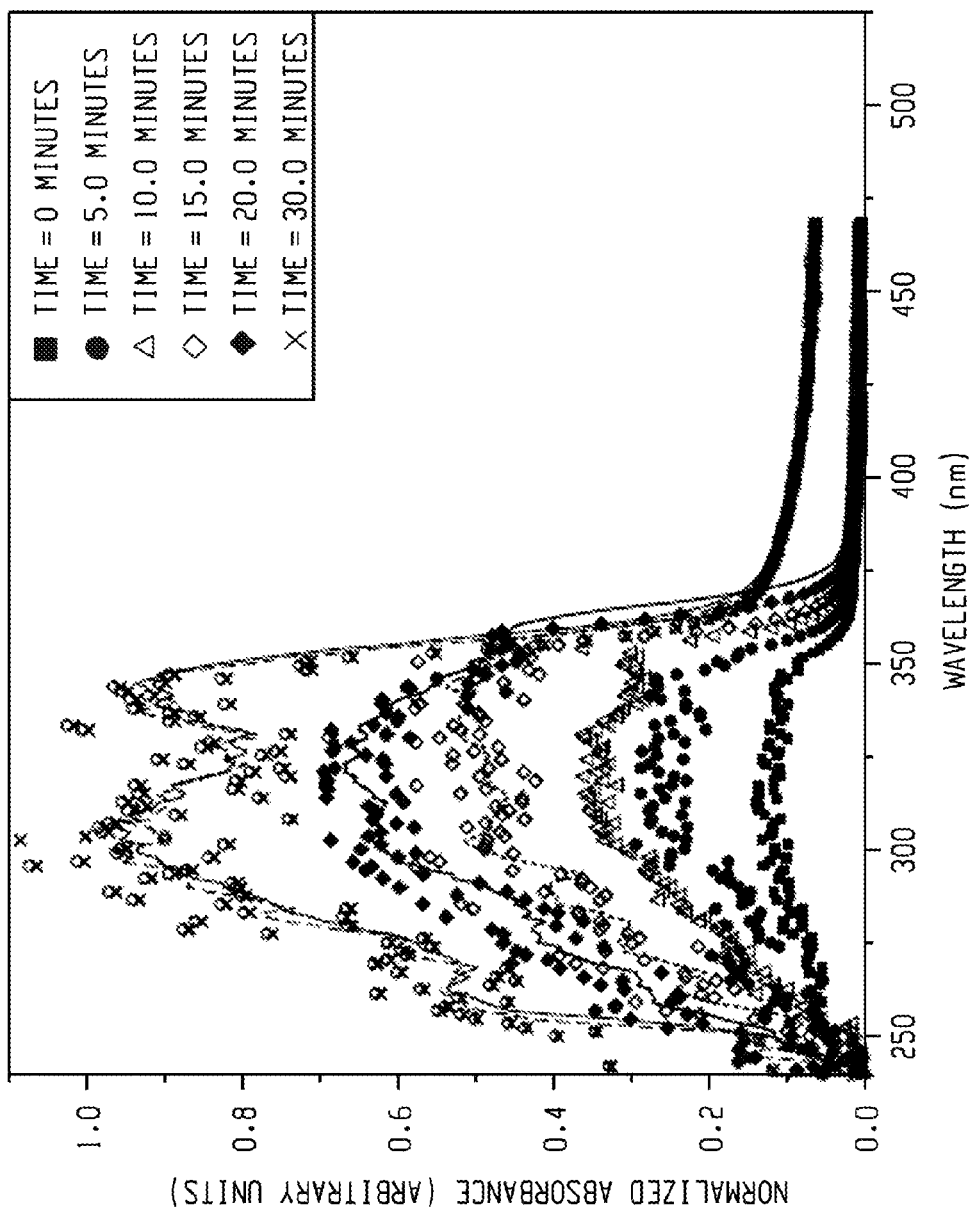
Figure 6:
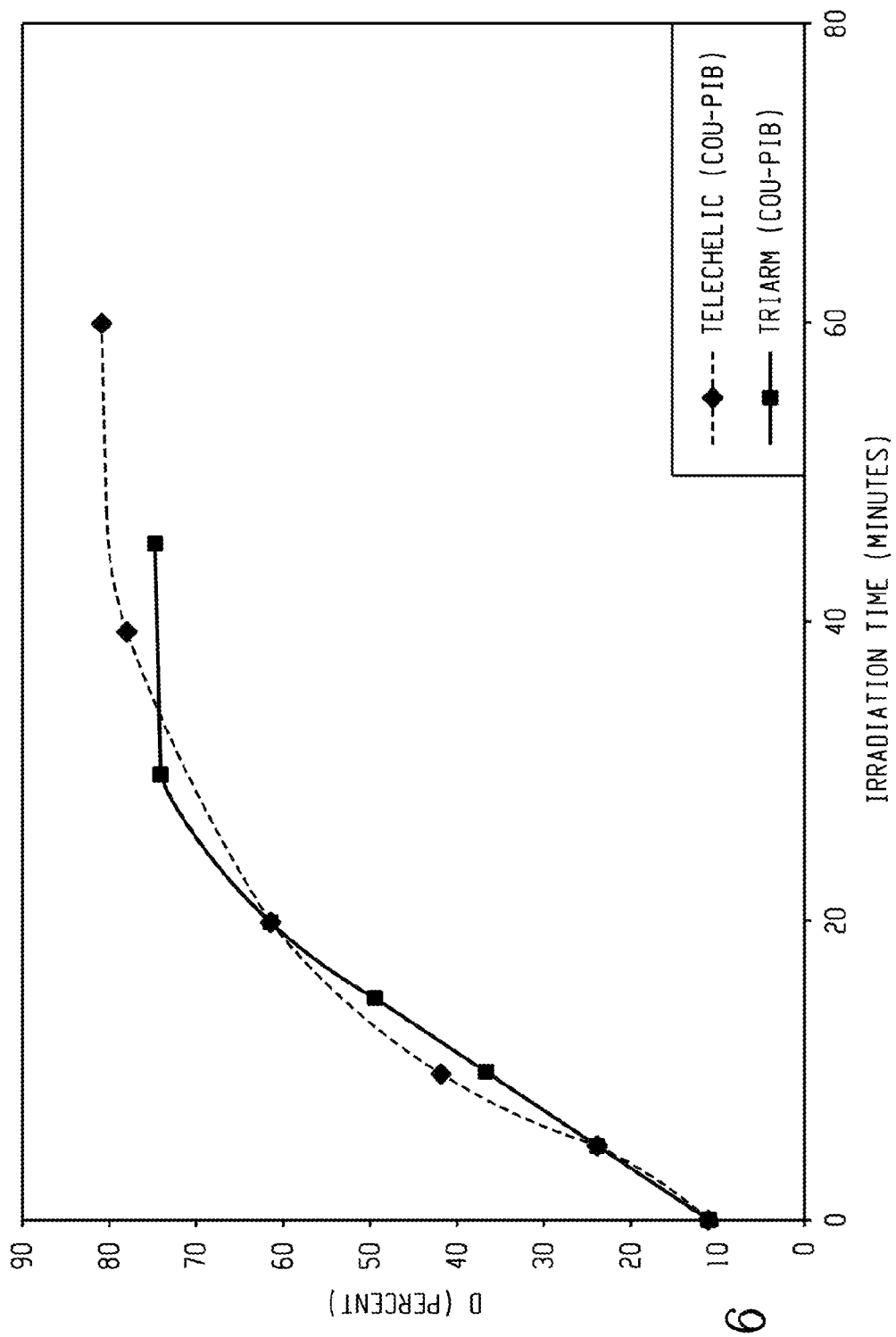
FIG. 6 is a plot of degree of crosslinking as a function of irradiation time for (COU-PIB)$_2$ and (COU-PIB)$_3$; the irradiation source was a 254 nanometer medium pressure broad spectrum lamp.

On the other hand, it is well-known that the cyclobutane ring in the photodimer can be cleaved to regenerate coumarin by photoirradiation with short wavelength (<300 nanometers). FIGS. 5(a) and (b) show UV-visible spectra of (COU-PIB)$_2$ and (COU-PIB)$_3$ after irradiation for different times t with 254 nanometer irradiation. As expected, the $A_{320}$ value of both the polymer significantly increases with prolonged irradiation time, indicating that the cyclobutane ring of the coumarin photodimer is gradually cleaved to regenerate coumarin. However, a leveling off in the absorbance is observed after irradiation for 30-45 minutes and 40-60 minutes for (COU-PIB)$_3$ and (COU-PIB)$_2$, respectively which leads to a slightly lower final absorbance than that of original polymer without irradiation, indicating an incomplete photo cleavage of photoinduced cyclobutane. A plot of the photo cleavage degree (D*) values of (COU-PIB)$_2$ and (COU-PIB)$_3$ versus UV irradiation time t is shown in FIG. 6 for the photo scission process. The photo cleavage degree is determined by the following equation $$D^*=(1-D_t/D_0)\times 100$$

wherein $D_0$ and $D_t$ are the crosslinking degree when photo cleavage occurs for 0 and t minutes, respectively. The final photo cleavage degree was respectively 19% and 25% for (COU-PIB)$_2$ and (COU-PIB)$_3$ after 40 minutes of irradiation, as may be easily observed from FIG. 6. Interestingly, the (COU-PIB)$_2$ photo scission reaction has gone to maximum completion than compared to (COU-PIB)$_3$ but the rate of reverse reaction is higher for (COU-PIB)$_3$ as clear from the initial slope of the photo cleavage reaction. Further, FIGS. 5 and 6 suggest that only part of the photodimer can be reverted back to the starting material. This suggests that the higher coumarin content favors the photo scission reaction, which is similar to the results of photodimerization. Similar photodimerization/photo cleavage of 8000 gram/mole (COU-PIB)$_2$ was conducted. For the photodimerization, leveling off absorbance was achieved close to 30 minutes suggesting the rate of dimerization depends upon the mole % of coumarin.

Figure 7:
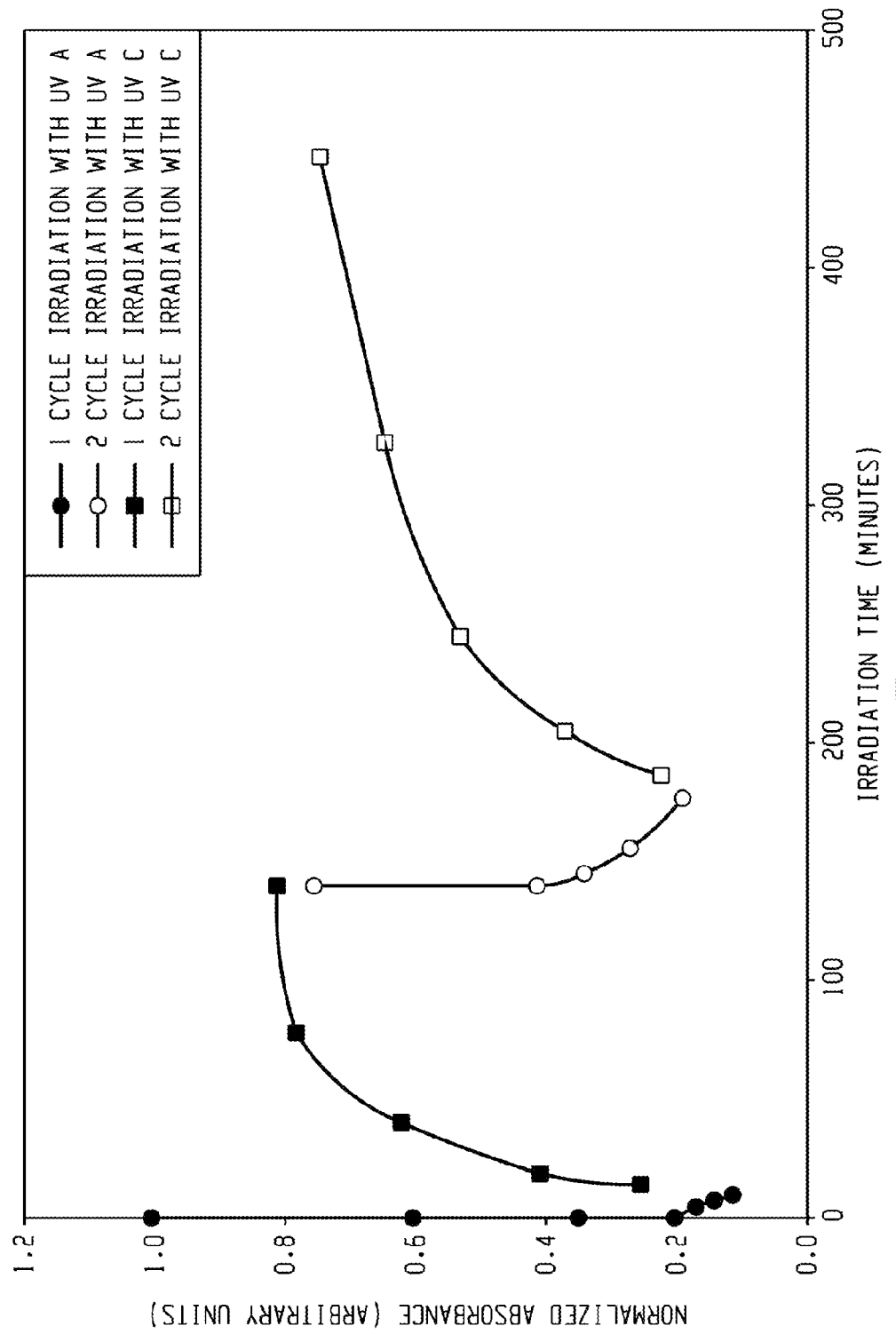
FIG. 7 is a plot of normalized absorbance versus irradiation time with UVA (circles; coumarin dimerization) and UVC radiation (squares; coumarin dimer reverting to coumarin) for a (COU-PIB)$_2$ of 2000 g/mol.
Figure 8A:
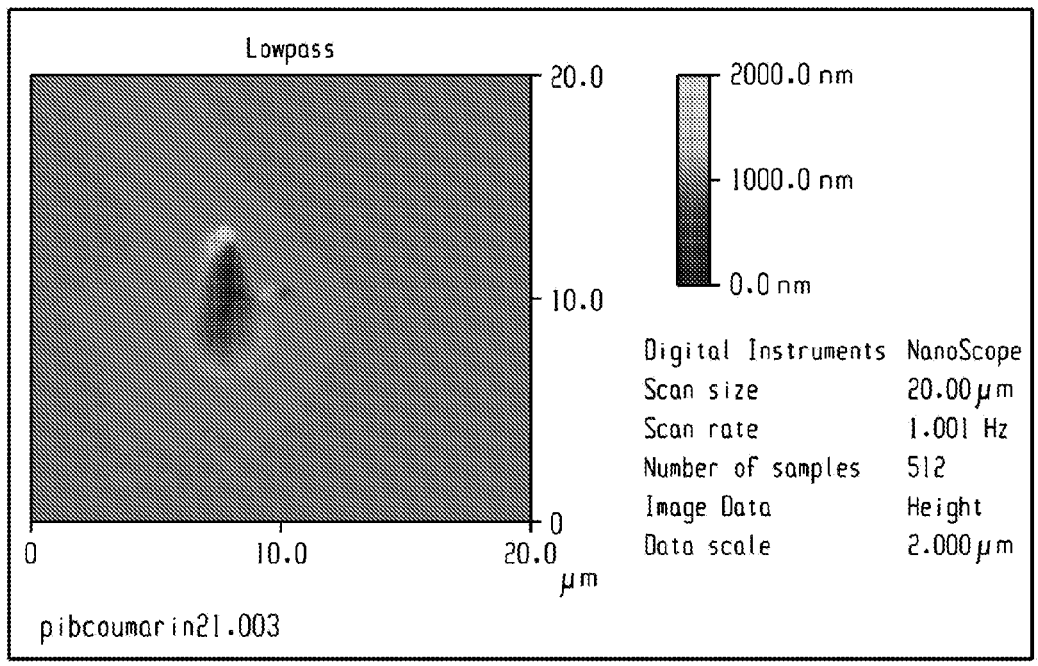
FIG. 8 shows the time-dependent change of height mode AFM images for a cut on the surface of a (COU-PIB)$_3$ film using high power UV lamp (a) time=0 minute, (b) time=30 minute; and (c) depth profile of cut at time=0 minute, and (d) depth profile of cut at time=30 minute.
Figure 8B:
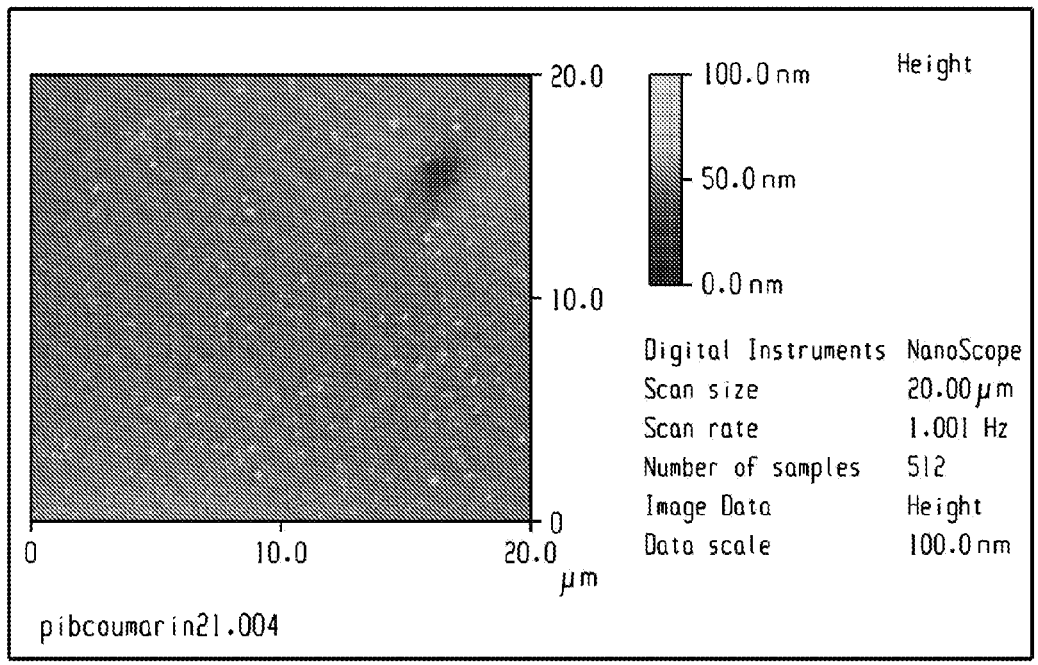
Figure 8C:
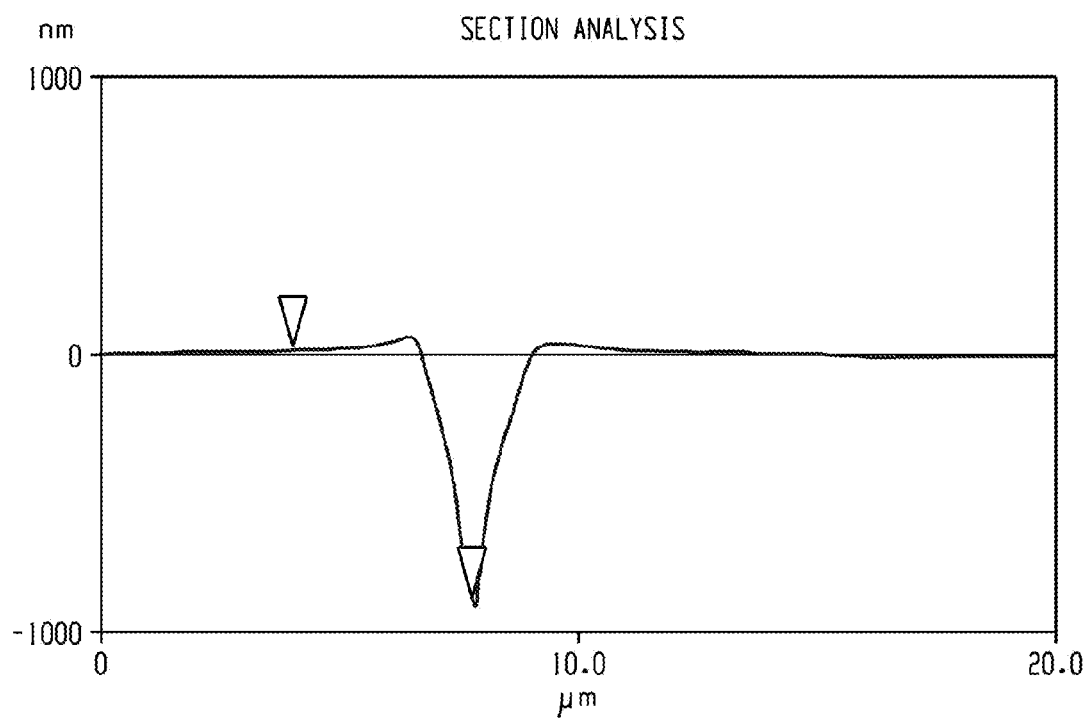
Figure 8D:
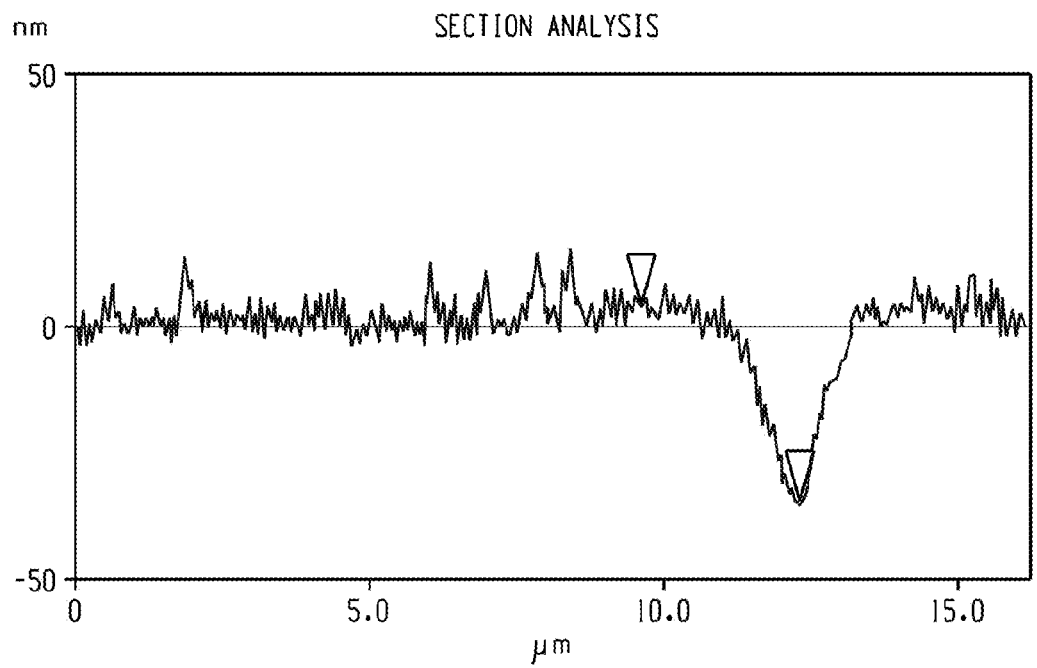
Figure 9A:
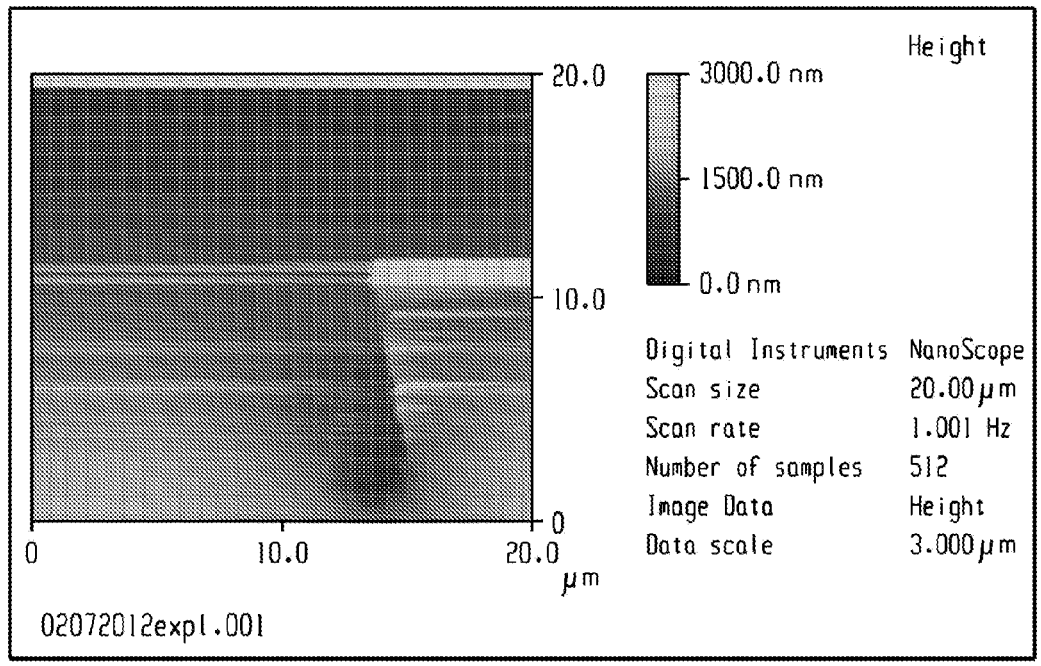
FIG. 9 shows the time-dependent change of height mode AFM images for a cut on the surface of a (COU-PIB)$_3$ film using low power UV lamp (a) time=0 minute, (b) time=40 minute; and (c) depth profile of cut at time=0 minute, and (d) depth profile of cut at time=40 minute.
Figure 9B:
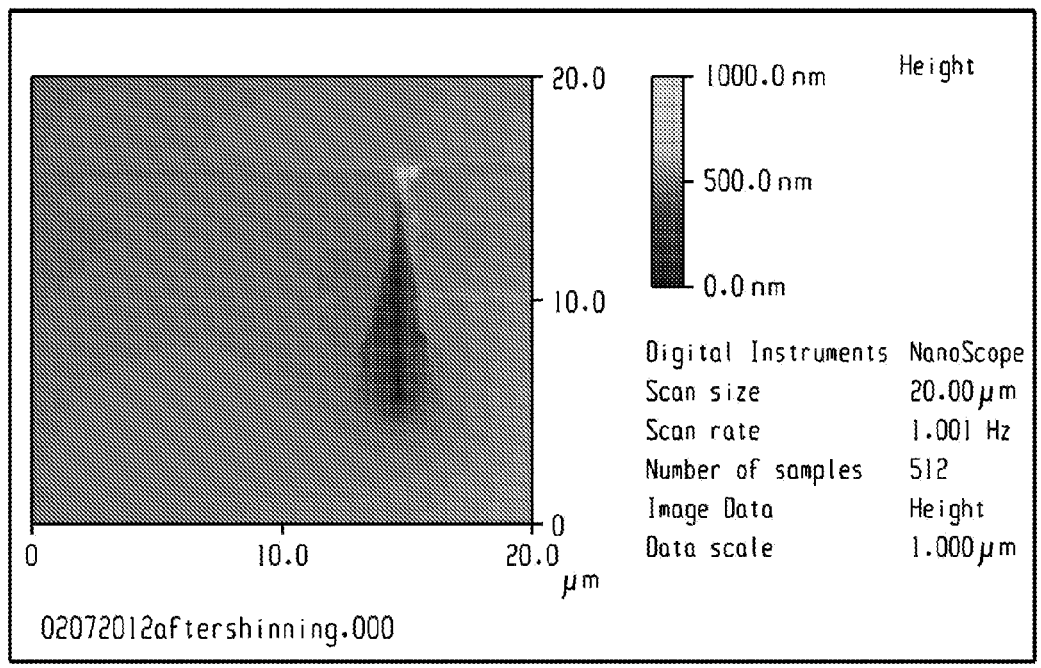
Figure 9C:
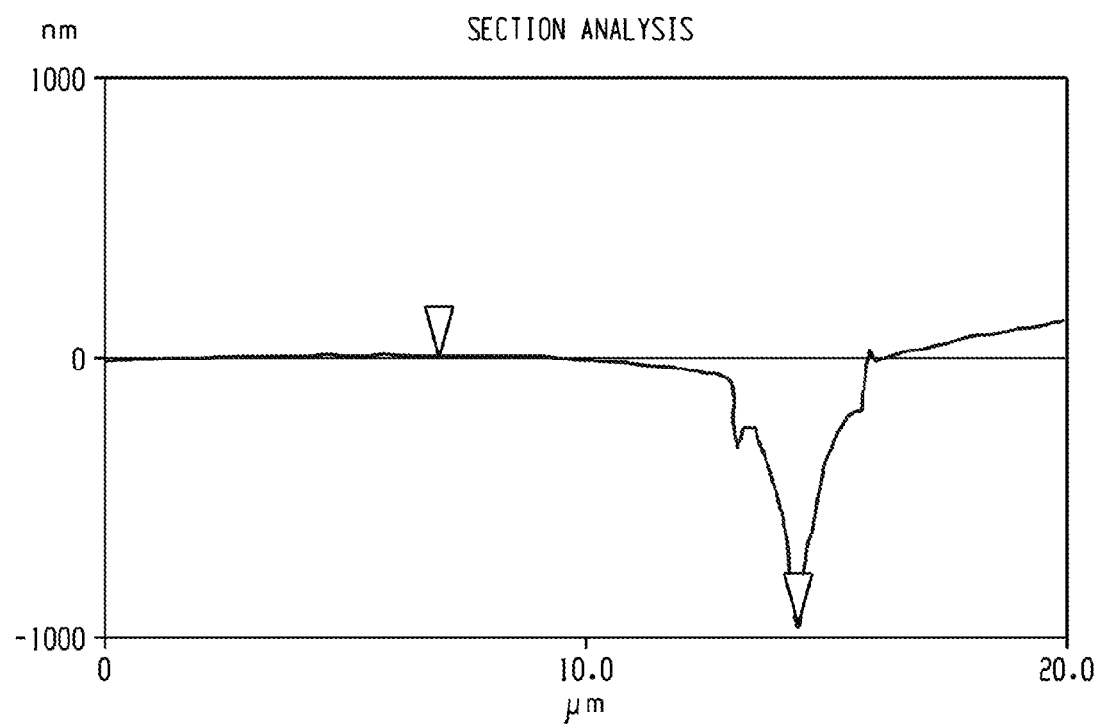
Figure 9D:
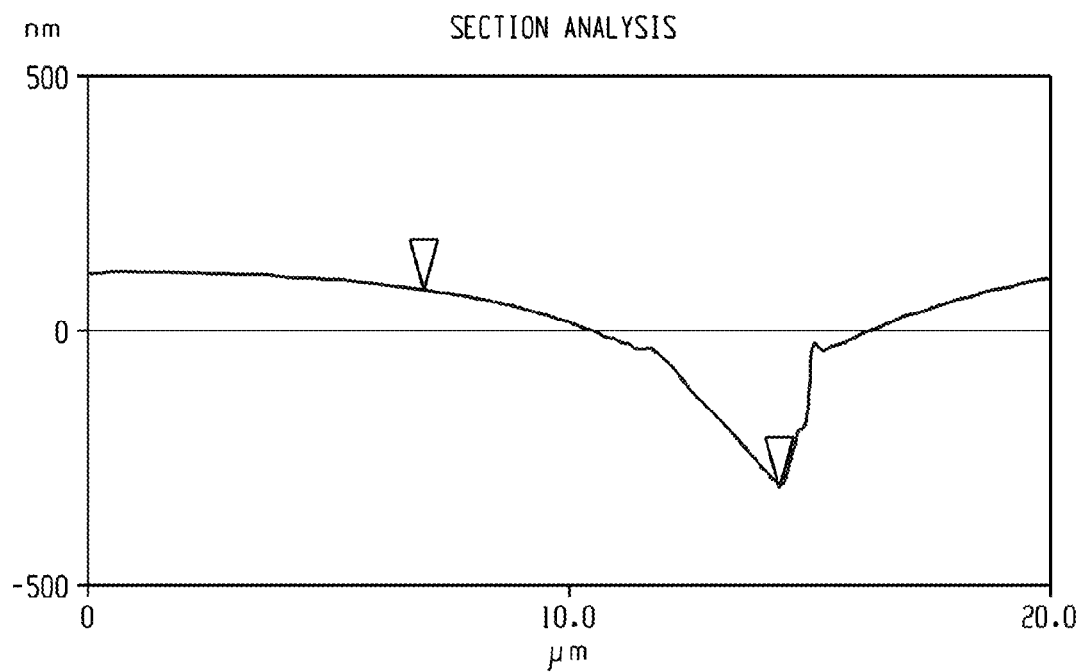
Figure 10A:
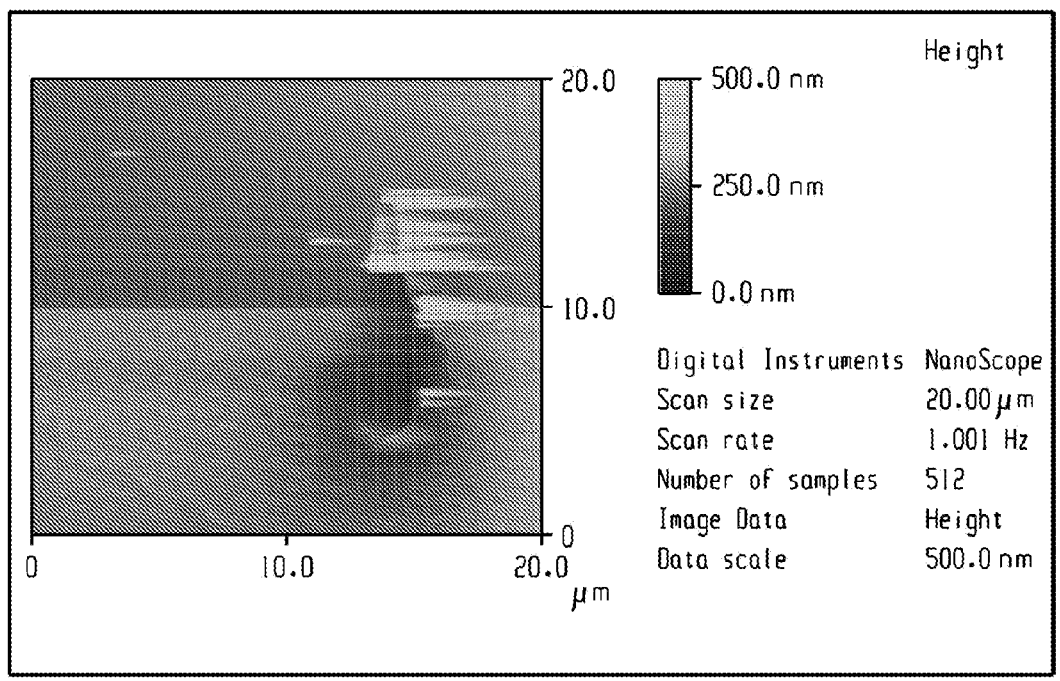
FIG. 10 shows the time-dependent change of height mode AFM images for a cut on the surface of a (COU-PIB)$_3$ film in the dark at (a) time=0 minute, (b) time=24 hours, and (c) time=48 hours; and (d) depth profile of cut at time=0 minute, (e) (d) depth profile of cut at time=24 hours, and (e) depth profile of cut at time=48 hours.
Figure 10B:
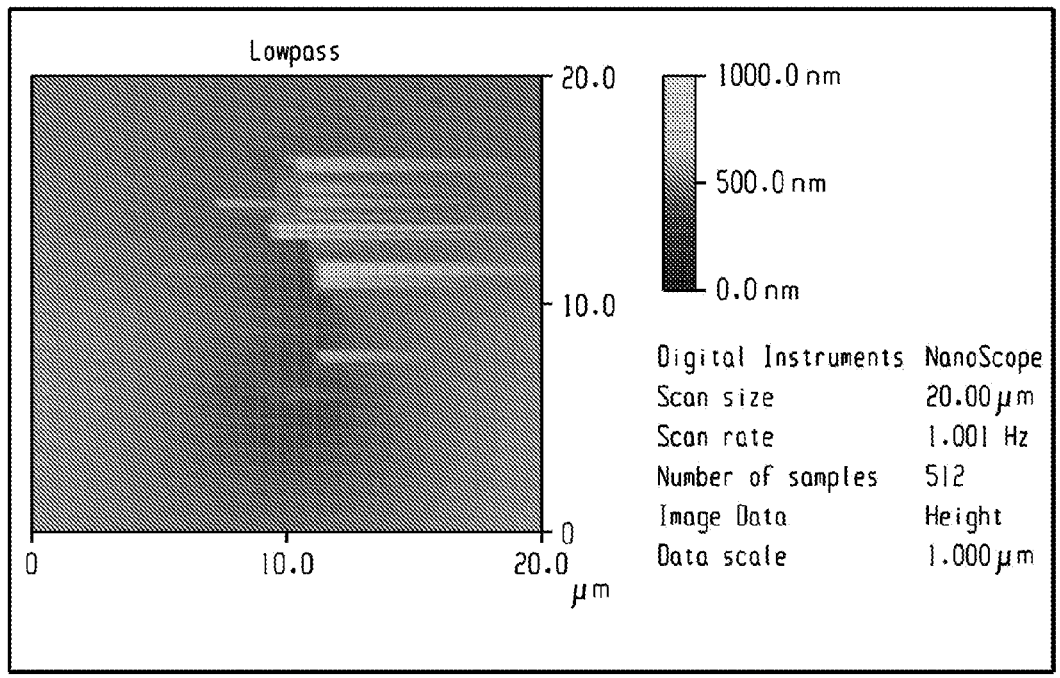
Figure 10C:
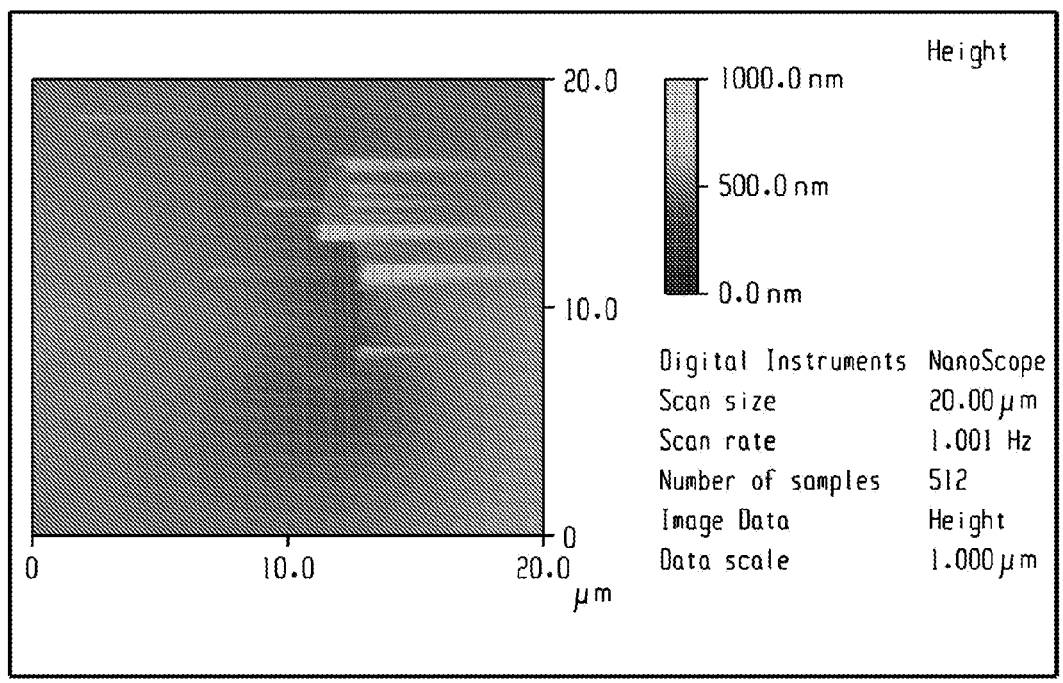
Figure 10D:
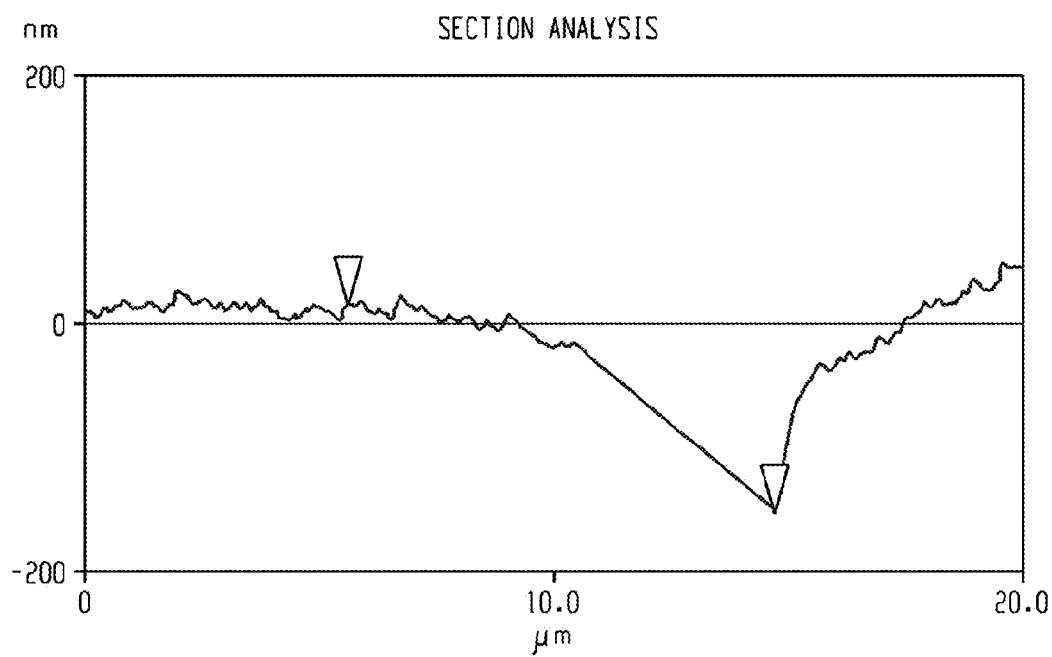
Figure 10E:
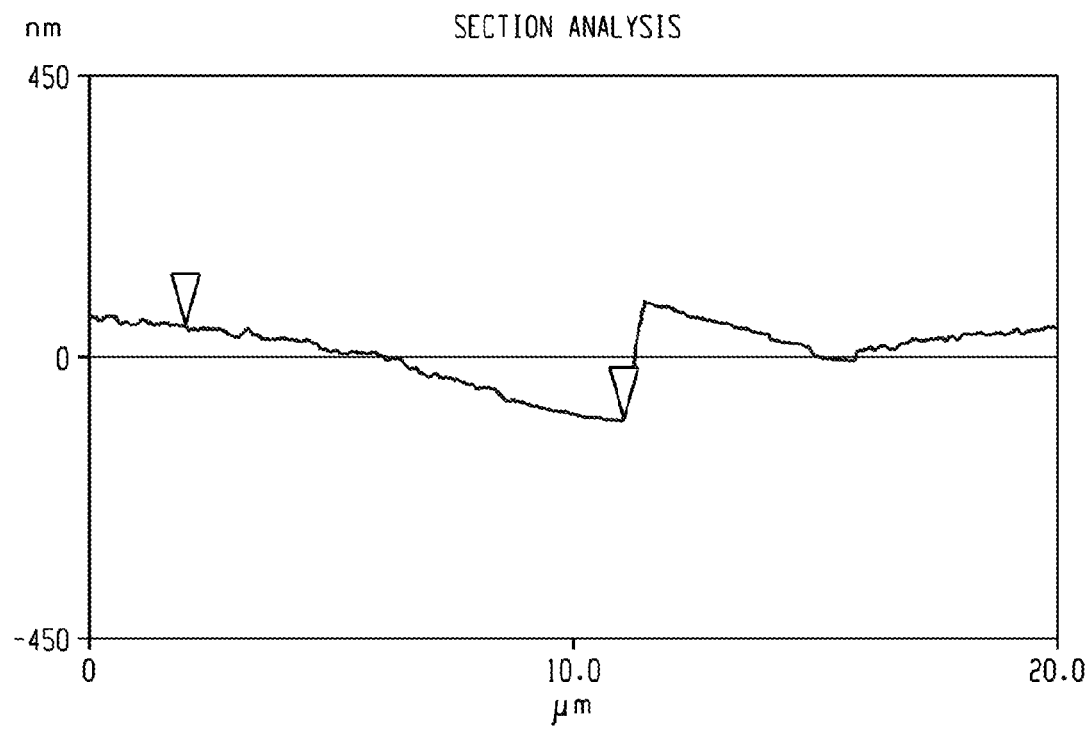
Figure 10F:
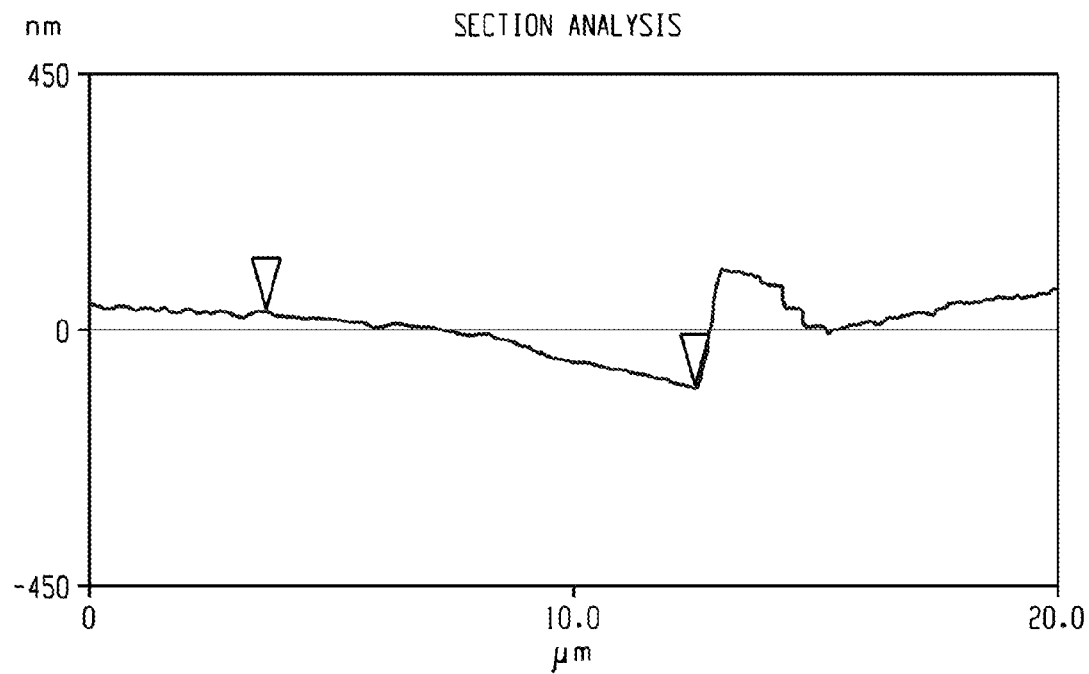

FIG. 7 shows the reversibility of the photodimerization/photo cleavage of the (COU-PIB)$_2$ utilizing UV-visible spectroscopy. The circles correspond to the chain/extension reaction due to UVA irradiation and the squares represent the photo cleavage reaction due to UVC irradiation, accompanied by reversal to the original (COU-PIB)$_2$. The photodimerization and photocleavage cycle was repeated twice with approximately 80% reversion after second cycle. The absorbance did not revert quantitatively due to a well-documented equilibrium between the dimer and cleaved coumarin at 254 nanometers.

Solvent cast films of (COU-PIB)$_3$ were scratched, then healed using UV irradiation of 254 and 365 nm. Contact mode AFM images were obtained before UV irradiation, and after, as shown in FIG. 8, using a high power UV lamp, or FIG. 9, using a low power UV lamp. FIG. 8($a$) shows a well-defined scratch in the film measuring 900 nanometers in depth. FIG. 8($b$) shows the same scratch with a depth of only 40 nanometers after irradiation for 30 minutes. Similarly, FIG. 9, (irradiation with low power UV lamp) shows progression of a scratch of depth 1460 nanometers to 390 nanometers after 40 minutes of UV irradiation at 254 and 365 nm. After a further 24 hours of irradiation, the scratch was completely healed.

FIG. 10 documents the control sample which was scratched using an AFM tip, then protected from light over 48 hours. The scratch depth shows some reduction from approximately 200 nanometers to 150 nanometers over the course of 48 hours, but significant healing is absent in the absence of UV irradiation.

The invention claimed is:

1. A compound of the following formula:

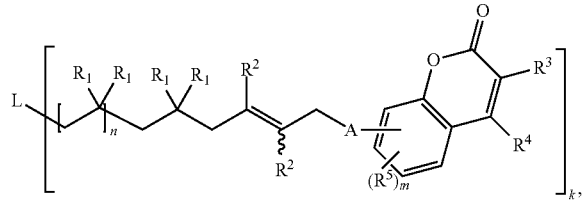

wherein:
L is a multivalent initiator residue;
k is an integer greater than or equal to 2;
A for each occurrence independently is selected from —NR$^a$—, —O—, or —OC(O)—, wherein R$^a$ is a H or a C$_1$-C$_4$ alkyl;
R$^3$, R$^4$, R$^5$ for each occurrence independently is each independently selected from H, C$_1$-C$_6$ alkyl, C$_2$-C$_6$ alkenyl, amino, C$_1$-C$_6$ alkoxy, —C(O)OR$^a$, hydroxy, or a halogen;
n for each occurrence independently is an integer not less than 2;
m for each occurrence independently is 0, 1, 2 or 3;
R$^1$ for each occurrence independently is H or a C$_1$-C$_4$ alkyl, a C$_1$-C$_6$ alkoxy or a substituted or unsubstituted aryl; and
R$^2$ for each occurrence independently is H, X$^2$, CH$_2$X$^2$, CHX$^2$$_2$, CX$^2$$_3$, CN, or NO$_2$, wherein X$^2$, for each occurrence, is independently a halogen.

2. The compound of claim 1, wherein
R$^1$ for each occasion is independently H or a C$_1$-C$_4$ alkyl; and
R$^2$ for each occasion is independently H.

3. The compound of claim 1, wherein
A for each occurrence independently is selected from —NR$^a$— or —O—;
m is 0; and
R$^3$ and R$^4$ is each independently selected from H, C$_1$-C$_6$ alkyl, or —C(O)OR$^a$.

4. The compound of claim 1, represented by the following structural formula:

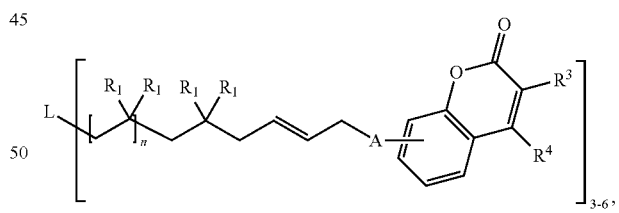

5. The compound of claim 1, represented by the following structural formula:

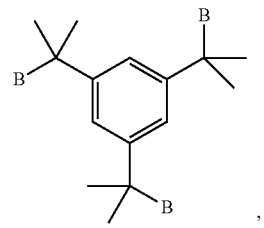

wherein

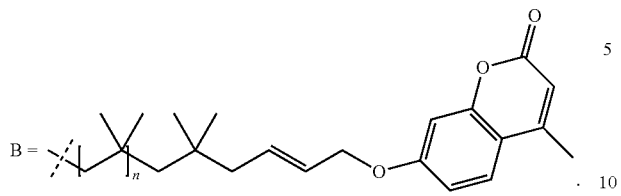

6. A method of synthesis of a compound of claim 1, comprising a step of reacting a compound represented by the following structural formula

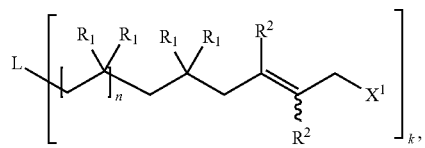

wherein $X^1$ is for each occurrence, independently, a halogen, with a compound of the following structural formula

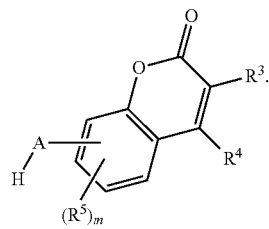

7. The method of claim 6, comprising the step of reacting the compound represented by the following structural formula

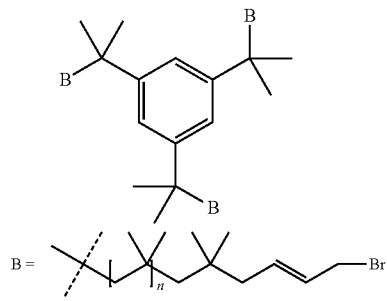

with the compound represented by the following structural formula:

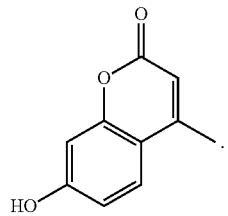

8. A dendritic polymer including repeating unit represented by the following structure formula:

$$L\text{-}Y\text{—}Z^2\text{—}Y\text{-}L,$$

wherein:

L is a multivalent initiator residue;

Y, for each occurrence independently, is represented by the following structural formula

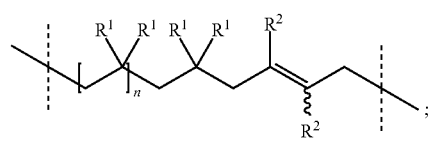

$Z^2$ is a dimer selected from

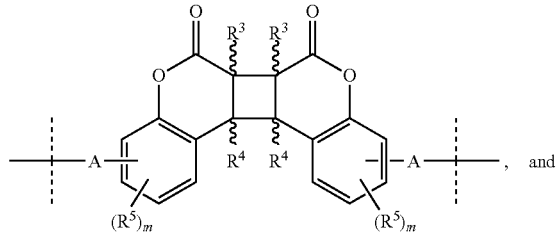, and

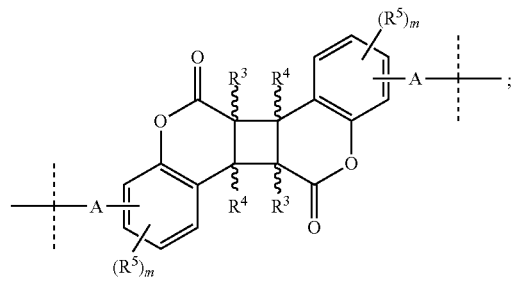;

and further wherein:

A for each occurrence independently is selected from —$NR^a$—, —O—, or —OC(O)—, wherein $R^a$ is a H or a $C_1$-$C_4$ alkyl;

$R^3$, $R^4$, $R^5$ for each occurrence independently is each independently selected from H, $C_1$-$C_6$ alkyl, $C_2$-$C_6$ alkenyl, amino, $C_1$-$C_6$ alkoxy, —$C(O)OR^a$, hydroxy, or a halogen;

n for each occurrence independently is an integer not less than 2;

m for each occurrence independently is 0, 1, 2 or 3;

$R^1$ for each occurrence independently is H or a $C_1$-$C_4$ alkyl, a $C_1$-$C_6$ alkoxy or a substituted or unsubstituted aryl; and $R^2$ for each occurrence independently is H, $X^2$, $CH_2X^2$, $CHX^2_2$, $CX^2_3$, CN, or $NO_2$, wherein $X^2$, for each occurrence, is independently a halogen.

9. The dendritic polymer of claim 8, wherein:

L is represented by the following structural formula:

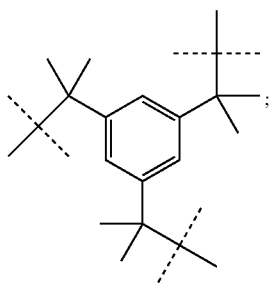

Y is represented by the following structural formula:

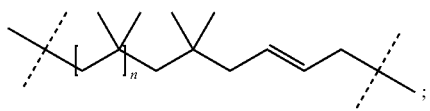

and $Z^2$ is a dimer selected from

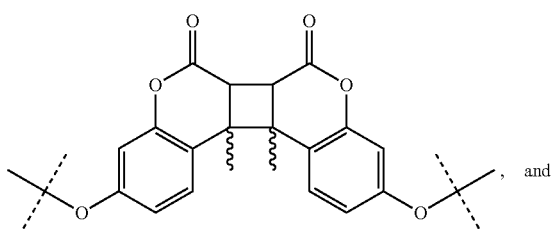

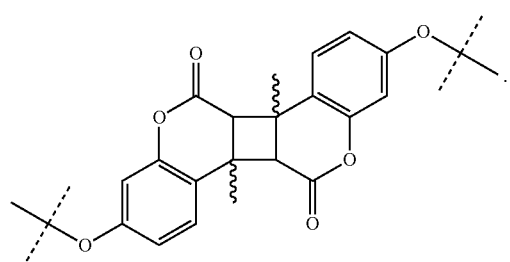

10. A method of synthesis of a dendritic polymer, the method comprising:

dimerizing a branched precursor represented by the following structural formula:

L-(Y—Z)$_k$ to produce a dendritic polymer including a repeating unit represented by the following structural formula:

L-Y—Z$^2$—Y-L, wherein:

L is a multivalent initiator residue;

k is an integer greater than or equal to 2;

Y, for each occurrence independently, is represented by the following structural formula

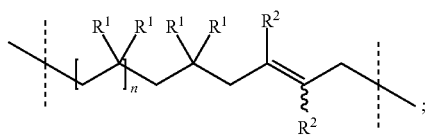

Z is represented by the following structural formula:

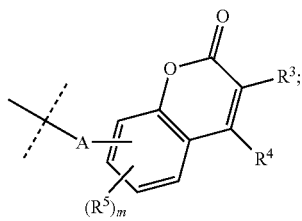

$Z^2$ is a dimer selected from

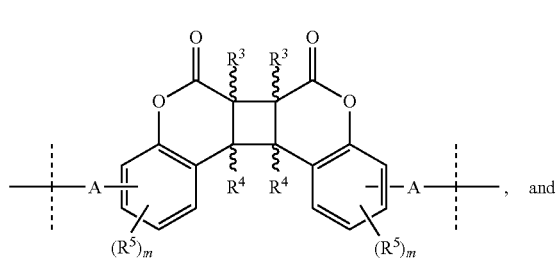

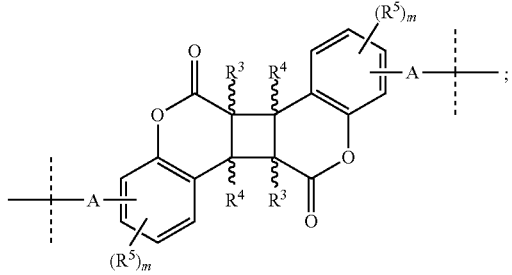

and further wherein:

A for each occurrence independently is selected from —NR$^a$—, —O—, or —OC(O)—, wherein R$^a$ is a H or a C$_1$-C$_4$ alkyl;

R$^3$, R$^4$, R$^5$ for each occurrence independently is each independently selected from H, C$_1$-C$_6$ alkyl, C$_2$-C$_6$ alkenyl, amino, C$_1$-C$_6$ alkoxy, —C(O)OR$^a$, hydroxy, or a halogen;

n for each occurrence independently is an integer not less than 2;

m for each occurrence independently is 0, 1, 2 or 3;

R$^1$ for each occurrence independently is H or a C$_1$-C$_4$ alkyl, a C$_1$-C$_6$ alkoxy or a substituted or unsubstituted aryl; and R$^2$ for each occurrence independently is H, X$^2$, CH$_2$X$^2$, CHX$^2{}_2$, CX$^2{}_3$, CN, or NO$_2$, wherein X$^2$, for each occurrence, is independently a halogen.

11. The method of claim 10, wherein dimerizing the branched precursor includes exposing the branched precursor to the ultraviolet radiation.

12. The method of claim 10, wherein:
L is represented by the following structural formula:

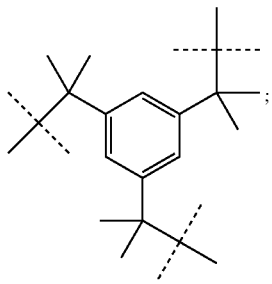

Y is represented by the following structural formula:

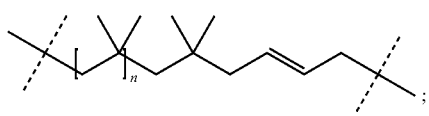

Z is represented by the following structural formula:

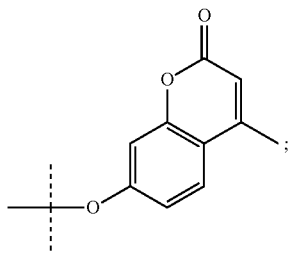

and
$Z^2$ is a dimer selected from

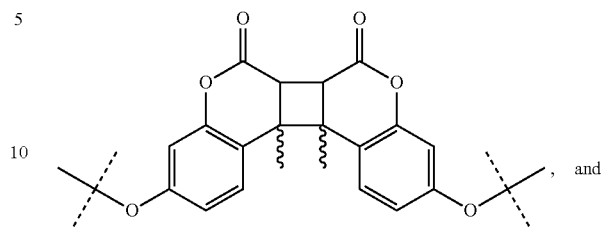, and

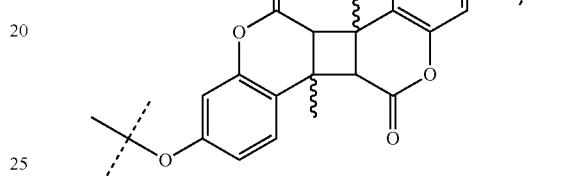.

13. An electronic device comprising an encapsulant or barrier layer comprising the compound of claim 1 or the dendritic polymer of claim 8.

14. The electronic device of claim 13, selected from a light emitting diode and a photovoltaic device.

* * * * *